(12) United States Patent
Furnas et al.

(10) Patent No.: US 8,094,293 B2
(45) Date of Patent: Jan. 10, 2012

(54) GLASS THICKNESS MEASUREMENT USING FLUORESCENCE

(75) Inventors: William J. Furnas, Elmira, NY (US); Sarath K. Tennakoon, East Granby, CT (US); Gary C. Weber, Horseheads, NY (US)

(73) Assignee: Emhart Glass S.A., Cham (CH)

( * ) Notice: Subject to any disclaimer, the term of this patent is extended or adjusted under 35 U.S.C. 154(b) by 262 days.

(21) Appl. No.: 12/535,850

(22) Filed: Aug. 5, 2009

(65) Prior Publication Data

US 2011/0032524 A1  Feb. 10, 2011

(51) Int. Cl.
*G01B 11/16* (2006.01)
(52) U.S. Cl. ............ 356/33; 356/35; 356/364; 356/630; 382/141; 382/142
(58) Field of Classification Search .................... 356/33, 356/35, 32, 364, 630; 382/141–142
See application file for complete search history.

(56) References Cited

U.S. PATENT DOCUMENTS 7,876,437 B1 * 1/2011 Furnas et al. ................. 356/364

OTHER PUBLICATIONS

Anton, Johan and Aben, Hillar, "A Compact Scattered Light Polariscope for Residual Stress Measurement in Glass Plates," Institute of Cybernetics. A poster presented at the Glass Processing Days show in Tampere, Finland, on Jun. 15-18, 2003.

* cited by examiner

*Primary Examiner* — Gregory J Toatley
*Assistant Examiner* — Iyabo S Alli
(74) *Attorney, Agent, or Firm* — Reinhart Boerner Van Deuren s.c.

(57) ABSTRACT

An apparatus and method for measurement of the stress in and thickness of flat glass or curved glass segments is disclosed that uses fluorescence to quickly and accurately ascertain both the thickness of the stress layers and the wall thickness in addition to the stress curve in flat glass or curved glass segments. The apparatus and method may be used to quickly and accurately measure both the stress in and the thickness of flat glass or curved glass segments at a plurality of various locations therein. The apparatus and method are adapted for large scale flat glass or curved glass segment manufacturing, and are capable of high speed measurement of the stress in and the thickness of the flat glass or curved glass segments.

25 Claims, 11 Drawing Sheets

GLASS THICKNESS MEASUREMENT USING FLUORESCENCE

IDENTIFICATION OF RELATED PATENT APPLICATIONS

This application is related to three other concurrently filed copending patent applications, namely U.S. patent application Ser. No. 12/535,821, entitled "Glass Container Stress Measurement Using Fluorescence," U.S. patent application Ser. No. 12/535,828, entitled "Glass Container Thickness Measurement Using Fluorescence," and U.S. patent application Ser. No. 12/535,836, entitled "Glass Stress Measurement Using Fluorescence," all assigned to the assignee of the present patent application, which three patent applications are each hereby incorporated herein by reference.

BACKGROUND OF THE INVENTION

Field of the Invention

The present invention relates generally to an apparatus and method for measurement of the stress across a thickness of glass such as in the walls of glass containers or in segments of flat glass, and more particularly for such an apparatus and method for using fluorescence to quickly and accurately ascertain both the thickness of the stress layers and the wall thickness in addition to the stress curve in glass containers or in segments of flat glass.

There are two broad categories of glass that is used in glass containers such as bottles, namely "hard" glass and "soft" glass. "Hard" glass, also called borosilicate glass, is made of silica and boron oxide, and requires much higher temperatures and is more difficult to form, and costs more than soft glass to manufacture, although it has excellent thermal stress characteristics. "Soft" glass, or soda-lime or soda-lime-silicate glass, is made of soda, lime, silica, alumina, and small quantities of fining agents, and may be manufactured at lower temperatures and is easier to form and cheaper to manufacture, although its thermal stress characteristics are not as good as hard glass. "Soft" glass is the more prevalent type of glass, and it is commonly used for glass containers.

For cost reasons, glass containers today are primarily made of soda-lime glass by molding molten glass into glass containers in blow molds. As the container leaves the mold and the glass cools, stress is induced in the glass, since the outside surfaces of glass containers cooled more rapidly and freeze while the inside surface and the interior walls are much hotter and are still flowing. The bottles are then run through an annealing process to remove these stresses.

The assignee of the present patent application has developed a process to thermally strengthen these glass containers. Instead of annealing the glass containers to remove stress, both the outside walls and the inside walls of the glass containers are rapidly cooled to produce heat strengthened soda lime glass containers which have intentionally introduced stress profiles across the walls of the glass container. There are compressive stresses on both the inside walls and the outside walls of the glass container, and tensional stress in the interior of the walls of the glass container.

Thermally strengthened soda lime glass containers that have the stress characteristics mentioned above are substantially stronger and more durable, and are much less likely to break when subjected to mechanical loading or handling or a sudden temperature change. Thus, the improved stress characteristics that are produced through the use of the improved cooling technology referenced above result in thermally strengthened glass containers that have been manufactured from soda lime glass.

While the improved glass container manufacturing technology referenced above consistently produces thermally strengthened soda lime glass containers having excellent stress characteristics, those skilled in the art will at once understand that it is necessary to inspect and verify the characteristics of the glass containers produced using this technology, including the stress characteristics of the glass containers. Inspecting the stress characteristics of the wall of a thermally strengthened soda lime glass container requires being able to make a highly accurate determination of the stress throughout the thickness of the wall of each glass container. While various optical and mechanical techniques are well known to locate physical imperfections in glass containers such as small cracks in the glass referred to as checks, foreign inclusions referred to as stones, bubbles in the glass referred to as blisters, and excessively thin walls, it is substantially more difficult to inspect the stress characteristics of the walls of glass containers.

Measurement of the stress characteristics of glass containers has been accomplished by the inventors using an Immersion light Polariscope ("IP") that requires the immersion of the glass container being inspected into a large container of optical index-matched fluid. Such a device is available from GlasStress Ltd. and is identified as their Automatic Transmission Polariscope AP-07. A light source shines a parallel polarized beam through the large container such that the beam travels tangentially through the side wall of the glass container (passing through the side wall of the glass container), where the beam crosses the axial stress field inside the side wall of the glass container and change its polarization characteristics as it passes through different stress layers across the side wall.

A camera is used to observe the intensity of the polarized component of the beam that passes through the side wall of the glass container. By observing the intensity of the beam as the polarization of the incoming beam is rotated, and by taking multiple images for each polarization, a determination may be made of the stress in the side wall of the glass container. Unfortunately, this Immersion light polariscope technique requires a glass container to be immersed in an optical index-matched fluid, which is not conducive to a large scale manufacturing inspection technique. Additionally, the measurement is not a fast measurement, but instead is relatively time-intensive, which also makes the technique unusable on a large scale manufacturing basis.

Another device available from GlasStress Ltd. is their Scattered Light Polariscope SCALP-03, which performs through-the-thickness stress measurement in architectural glass panels and automotive glazing. This device takes five seconds for a single measurement, works only with limited glass surfaces, and is inherently unsuitable for application in a mass production environment. The operational theory used by this device is discussed in "A compact Scattered Light Polariscope for Residual Stress Measurement in Glass Plates," Johan Anton and Hillar Aben, a poster presented at the Glass Processing Days show in Tampere, Finland, on Jun. 15-18, 2003. To summarize, it uses the scattering of a polarized light beam from a laser as it passes through the glass, and rotates this light beam to rotate its polarization to obtain an amplified signal.

It is accordingly desirable to provide an apparatus capable of measuring the thickness of flat glass or curved glass segments as well as a related method of measuring the thickness of the of flat glass or curved glass segments. It is also desirable that such an apparatus be adaptable for large scale glass manufacturing, such that it would be capable of high speed measurement of the thickness of the flat glass or curved glass segments. As such, it desirable that such an apparatus not require that the flat glass or curved glass segments be immersed during the inspection process, thereby not increasing the difficulty of handling of the flat glass or curved glass segments being inspected.

It is further desirable that such an apparatus be capable of producing highly accurate determinations of the thickness of the flat glass or curved glass segments. It would also be beneficial if such an apparatus be capable of measuring the thickness of each of the stress layers in the flat glass or curved glass segments. In so doing, it would be desirable that such an apparatus also be capable of measuring the stress in the flat glass or curved glass segments. Such an apparatus preferably should further be capable of quickly and accurately measuring both the thickness of and the stress in the flat glass or curved glass segments throughout the entirety of the flat glass or curved glass segments.

Such an improved glass thickness measurement apparatus should be of a construction which is both durable and long lasting, and it should also require little or no maintenance to be provided by the user throughout its operating lifetime. In order to enhance the market appeal of such a glass thickness measurement system, is should preferably be of relatively inexpensive construction to thereby afford it the broadest possible market. Finally, it would also be beneficial it all of the aforesaid advantages and benefits of such a glass thickness measurement apparatus and method be achieved without incurring any substantial relative disadvantage.

SUMMARY OF THE INVENTION

The disadvantages and limitations of the background art discussed above are overcome by the present invention. With this invention, linearly polarized light from a laser is coupled into the side wall of a glass container at an optimal angle with respect to the side wall of the glass container in order to obtain an optimum (maximum intensity) fluorescence signal within the side wall of the glass container. This may be accomplished by using a right angle isosceles coupling prism (also referred to as a 45 degree –45 degree –90 degree prism) that is optical glass and is located with the longitudinal axis of its hypotenuse (its longest side) located tangentially with respect to the side wall of the glass container, and using fluid coupling between the coupling prism and the outside wall of the glass container. The linearly polarized laser beam is directed into the coupling prism through one of the shorter sides of the coupling prism.

The linearly polarized laser beam thus enters the side wall of the glass container from the outside to the glass container, and, as it enters and passes through the side wall of the glass container, the linearly polarized laser beam excites the electronic states of some of the elements and produces fluorescent light along its path. This fluorescent light source along the path in the side wall of the glass container allows the stress within the side wall of the glass container to be determined. Part of this fluorescent light is linearly polarized on a plane perpendicular to the laser polarization and propagation path.

As this linearly polarized light travels though the stress field in the side wall of the glass container, it changes its polarization characteristics from linear to elliptical to circular to elliptical to linear, which pattern is repeated. (It should be noted that for typical wall thicknesses in glass containers the magnitude of the polarization change likely never gets all the way to circular polarization. The apparatus technique of the present invention thus would not need to be able to handle the "wrap around" in signal level that would happen should it in fact go through circular polarization.) The linearly, circularly, or elliptically polarized fluorescence light exits the outside wall of the glass container and travels through the coupling fluid to the coupling prism and exits the other of the shorter sides of the coupling prism.

The exiting linearly, circularly, or elliptically polarized fluorescence light that has passed through the stress field in the glass wall is then converted to linearly polarized components by a quarter wave plate. The quarter wave plate is rotated so that the fast axis of the quarter wave plate is aligned with the initial polarization plane (from the fluorescence) of the incident light. The linearly polarized components of light then pass through a ferroelectric liquid crystal ("FLC") rotated at 45 degrees to the quarter wave plate that is alternately driven at two different voltages that cause the FLC to alternately pass each component of the fluorescence light.

A camera having a bandpass filter that blocks the laser light and passes fluorescent bandwidths alternately images the linearly polarized light passed through the FLC at plus and minus 45 degrees from the axis of the quarter wave plate to produce alternating plus and minus 45 degree images having two polar rotations that are 90 degrees apart. The difference between alternating images is divided by sum of the two images to produce a normalized difference image, which has a line the intensity variation of which is representative of the polarization changes from stress effects to the fluorescence light emitted from each point along the laser beam in the side wall of the glass container. (It should be noted that if there is no stress, there is no intensity variation in the difference over sum normalized image.)

By plotting the intensity along this line, a nominally rotated S-shaped retardance curve may be obtained by curve fitting a polynomial which, when differentiated, produces a parabola that is representative of the stress across the thickness of the side wall of a properly thermally strengthened glass container at the location being tested. In the glass thickness measurement system of the present invention, following proper calibration, the length of the light line is proportional to the thickness of the side wall of the glass container. The stress parabola indicates both the type and magnitude of the stress within the side wall of the glass container, with compression being indicated by a negative value in the stress parabola and tension being indicated by a positive value in the stress parabola. Accordingly, both the stress within the side wall of a glass container as well as the thickness of side wall of the glass container may advantageously be determined using the glass thickness measurement system and method of the present invention.

Once calibrated, the glass thickness measurement system and method of the present invention can quickly determine the stress and the thickness of the side wall of a glass container. In an exemplary embodiment, the glass container may be rotated approximately twenty degrees between readings. For this embodiment, the glass container will be rotated to take eighteen readings that are each twenty degrees apart, thereby fully inspecting the wall thickness and stress of the side wall of the glass container throughout the circumference of the glass container. Glass containers not falling within appropriate ranges of wall thickness and stress may be discarded and recycled.

The glass thickness measurement system and method of the present invention is relatively simple to install in the cold end inspection process. A low volume coupling liquid fluid stream may be supplied to fill the coupling prism—glass container sidewall interface, with the liquid coupling fluid being collected by a pan located below the glass thickness measurement apparatus. The liquid coupling fluid used will be a liquid that has an index of refraction close to the that of glass; one acceptable coupling fluid that may be used, for example, is water. Since the required readings and rotations may be performed very quickly, implementation of the glass thickness measurement system and method of the present invention into a high volume glass container manufacturing and inspection line is quite feasible.

Alternatively, light may be coupled into and out of the glass container using air as a coupling fluid to fill the coupling prism—glass container sidewall interface. While air may have a coupling efficiency that is less than that of an optimal liquid coupling fluid, it will at once be appreciated by those skilled in the art that the use of air rather than a liquid coupling fluid will present decided advantages in the logistics of a high speed inspection process in that the entire liquid supply, recovery, and recirculation apparatus is not necessary when using air as the coupling fluid. This thereby facilitates taking the required readings and rotations very quickly and without wetting the glass containers being inspected, thus further enhancing the implementation of the glass thickness measurement system and method of the present invention into a high volume glass container manufacturing and inspection line.

The glass thickness measurement system and method of the present invention is also applicable to measuring the stress distribution across thermally hardened flat glass or curved glass segments, and is capable of quickly and accurately measuring both the stress in and the thickness of the walls of flat glass or curved glass segments. The coupling fluid used to couple light into and out of flat glass or curved glass segments may be either a liquid or air. If a liquid is used, it may be applied in a thin layer to flat glass being inspected or, alternately, sprayed in a light mist onto the surface of the flat glass or curved glass segments.

It may therefore be seen that the present invention teaches a glass thickness measurement system as well as a related method of measuring the stress in the side walls of glass containers or flat glass or curved glass segments. The glass thickness measurement system and method of the present invention are adaptable for large scale glass container or flat glass or curved glass segment manufacturing, and they are thus capable of high speed measurement of the stress in the side walls of glass containers of flat glass or curved glass segments. The glass thickness measurement system and method of the present invention also do not require that the glass containers or flat glass or curved glass segments be immersed in liquid during the inspection process, thereby not increasing the handling of the glass containers or flat glass or curved glass segments being inspected.

The glass thickness measurement system and method of the present invention produce highly accurate determinations of the stress in the side walls of glass container or in flat glass or curved glass segments. The glass thickness measurement system and method of the present invention are also capable of measuring the thickness of each of the stress layers in the sidewalls of glass containers or in flat glass or curved glass segments. The glass thickness measurement system and method of the present invention are capable of measuring the wall thickness of the side walls of glass containers or the flat glass or curved glass segments. The glass thickness measurement system and method of the present invention are capable of quickly and accurately measuring both the stress in and the thickness of the side walls of glass containers throughout the circumference of the glass containers or in a plurality of positions in the flat glass or curved glass segments.

The glass thickness measurement system of the present invention is of a construction which is both durable and long lasting, and it should also require little or no maintenance to be provided by the user throughout its operating lifetime. The glass thickness measurement system of the present invention is also be of relatively inexpensive construction to enhance its market appeal and to thereby afford it the broadest possible market. Finally, the glass thickness measurement system and method of the present invention achieves all of the aforesaid advantages and objectives without incurring any substantial relative disadvantage.

DESCRIPTION OF THE DRAWINGS

These and other advantages of the present invention are best understood with reference to the drawings, in which.

DETAILED DESCRIPTION OF THE EXEMPLARY EMBODIMENTS

Figure 1:
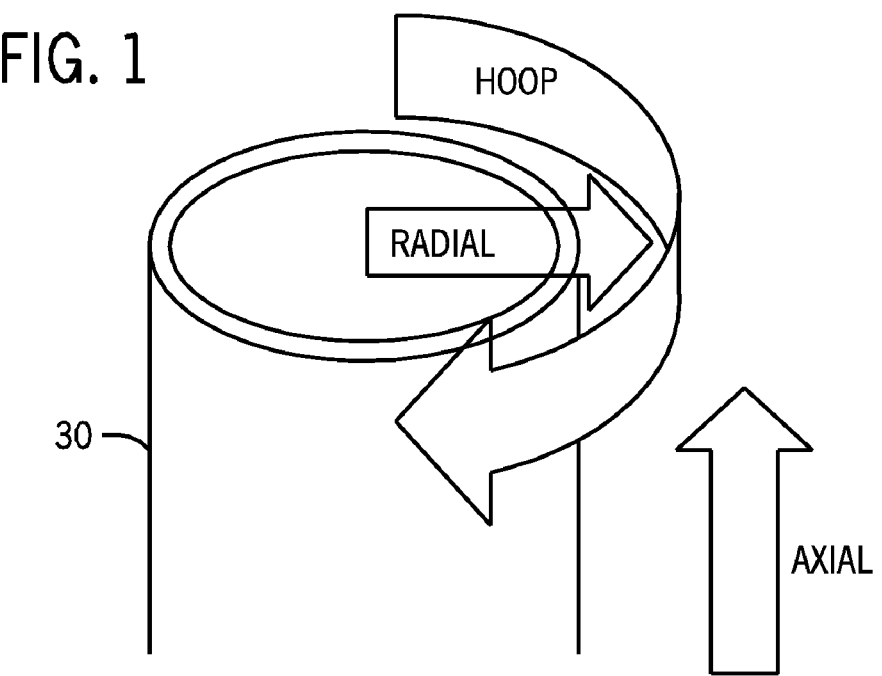
FIG. 1 is an isometric depiction of the lower half of a glass container schematically illustrating a three dimensional coordinate system within the glass container for discussing the stress field.

Prior to discussing exemplary embodiments of the glass thickness measurement system and method of the present invention, a brief discussion of some of the principles used by the present invention will be provided. Referring first to FIG. 1, a coordinate system for three dimensional stress in a glass container 30 (the lower portion of which is illustrated in FIG. 1) is provided. Radial stress is defined across the wall of the glass container 30, in a first of three relatively orthogonal directions. Hoop stress is defined around the circumference of the glass container 30, in a second of the three relatively orthogonal directions. Axial stress is defined along the height of the glass container 30, in a third of the three relatively orthogonal directions.

The thermal strengthening of the glass container 30 in rapidly cools the inner and outer surfaces of the glass container 30 until the inner and outer surface temperatures are below the glass transition temperature, thereby freezing the surface structure of the glass container 30 while allowing the inner glass to continue to flow until its temperature reaches the glass transition temperature, then letting the glass container 30 cool to room temperature. This process enhances the stress characteristics of the glass container 30, making it substantially stronger and more durable. When the container reaches room temperature, the inner and outer surfaces of the glass container 30 will be in compression and the interior of the walls of the glass container 30 will be in tension. In a properly controlled cooling process, the magnitude of the hoop stress and the axial stress at the surface of the glass container 30 (and indeed at any point across the thickness of the walls of the glass container 30) should be nearly equal. The stress along the thickness of the walls of the glass container 30 should thus vary from compression at the outer walls to tension in the interior of the walls to compression at the inner walls, with very little or no net radial stress.

The glass thickness measurement system and method of the present invention uses the fluorescent light produced by a laser beam passing through the wall of a glass container as a linear polarized light source in order to determine the stress in the wall of the glass container. As polarized light passes through stressed glass, the phase of the light will change as it goes through the stress field. Linearly polarized fluorescent light emitted from along the entire laser beam path inside of the wall of a glass container will become elliptically or circularly polarized as it pass through the stressed wall of the glass container.

The glass thickness measurement system and method of the present invention uses the optical principle that normally transparent isotropic substances are made optically anisotropic by the existence of internal stresses therein. This phenomenon, known as stress birefringence, exists as the difference in refractive index between two orthogonally polarized modes, and will vary from point to point throughout the wall of a glass container as the stress in the wall of the glass container varies. Retardance is the difference in optical path length between the two orthogonally polarized modes, and the present invention will determine the retardance along the light path within the wall of a glass container from the intensity of the emitted fluorescent light from along the entire laser beam path within the wall of the glass container in the two orthogonally polarized modes.

The viewing angle and the angle of polarization being emitted from the fluorescence are chosen to maximize the difference between the two orthogonally polarized modes being evaluated within the constraints of the improvements described. Referring back to FIG. 1 for the moment, by viewing at 45 degrees to a tangent of the hoop (the circumference of the glass container 30), the axial stress is fully acting in the vertical direction, but that angle means that the horizontal direction would be a partial combination of Hoop and Radial. Because of refraction effects discussed earlier, the angle can not be decreased to look tangentially as in the immersion polariscope.

Figure 2:
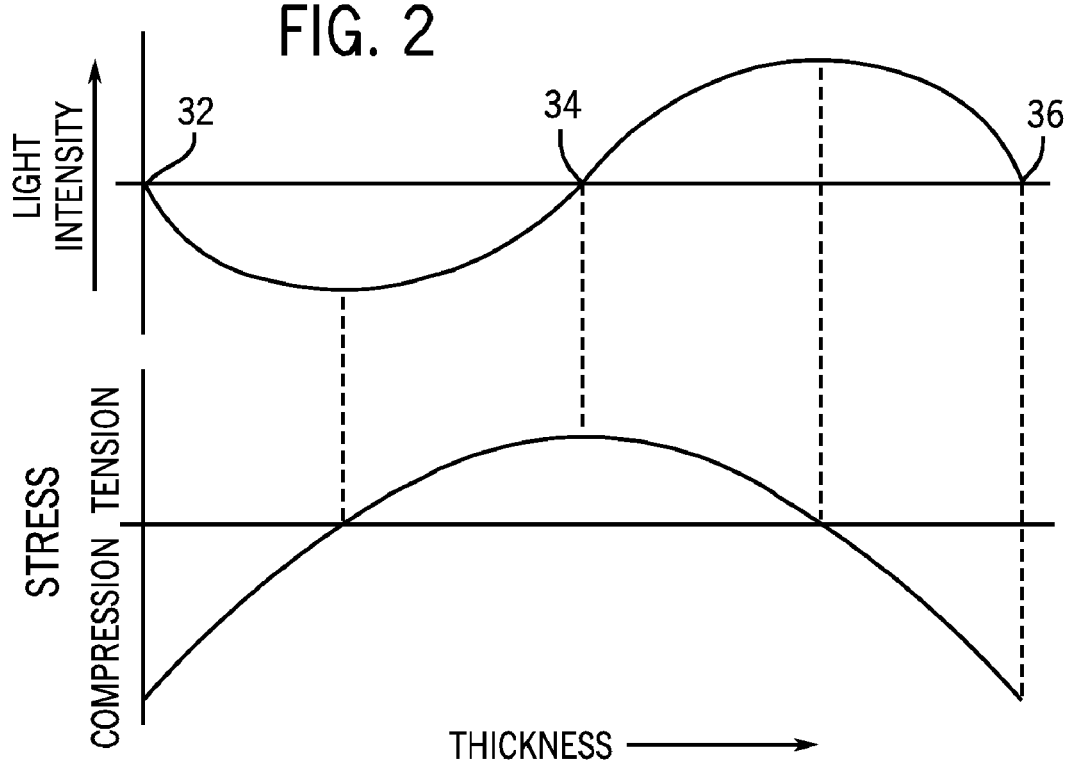
FIG. 2 is a light intensity curve analysis result related to the retardance in the path of the polarized light, located above a stress parabola, with both curves being plotted against the thickness of a side wall in a glass container having an optimal stress parabola.

Referring next to FIG. 2, two curves are shown, with the top curve being a plot of the retardance curve from an outside wall 32 to a midpoint of the wall 34 to an inside wall 36 of a glass container having an ideal stress distribution throughout its wall. Located below the retardance curve is a parabola having values that are the derivative of the values of the retardance curve. This parabolic curve is the stress parabola, and is a calculated plot of the stress from the outside wall 32 to the inside wall 36 of the glass container, and has an ideal stress distribution throughout its wall varying from compression at the outer wall 32 to tension in the interior of the wall (including the midpoint of the wall 34) to compression at the inside wall 36. Glass containers not having the proper characteristics are unacceptable, and the glass thickness measurement system and method of the present invention is designed to evaluate glass containers and determine the stress parabola in order to identify glass containers not having proper stress characteristics so that they may be discarded.

Figure 3:
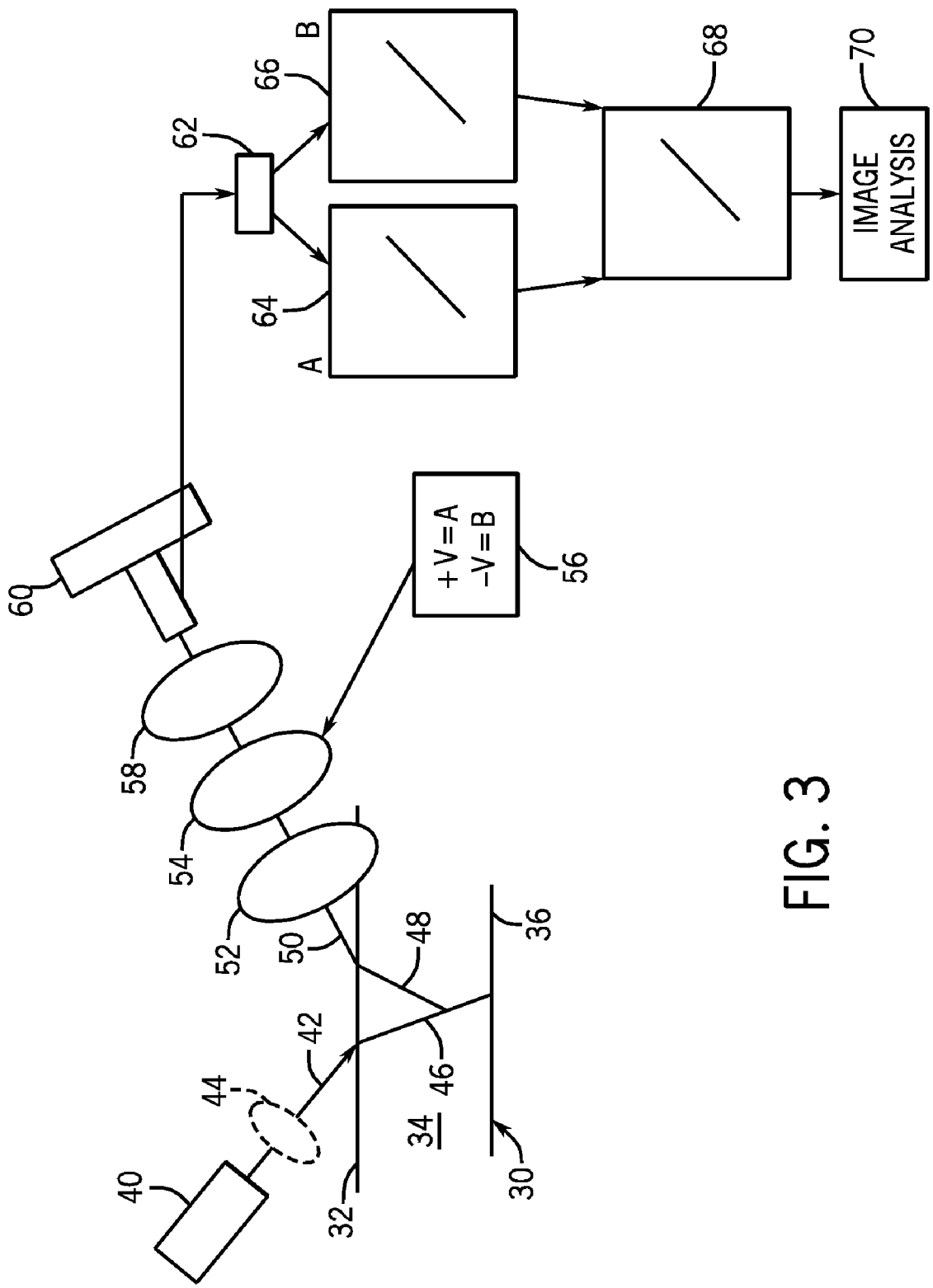
FIG. 3 is a diagram illustrating in highly schematic form the glass thickness measurement system of the present invention.

Referring now to FIG. 3, an exemplary embodiment of the glass thickness measurement system of the present invention is shown in highly schematic fashion with respect to a glass container 30. (It will be understood by those skilled in the art that the principles of operation demonstrated with respect to the example using the glass container 30 shown in FIG. 3 are equally applicable to flat glass or curved glass.) A laser light source 40 produces a linearly polarized light beam 42 that is coupled into the outside wall 32 of the glass container 30 at an optimal angle (to be discussed below). The laser light source 40 is either mounted in a manner permitting its rotation to rotate the polarization of the linearly polarized light beam, or, alternately, an optional half wave plate 44 may be used between the laser light source 40 and the outside wall 32 of the glass container 30 to rotate the polarization of the linearly polarized light beam 42 to the desired orientation. This polarization direction will be in a plane that is parallel to a plane that is orthogonal to the axis of fluorescent light exiting the side wall of the glass container 30 toward the CCD camera 60.

The linearly polarized light beam 42 refracts and enters into the side of the glass container 30, where it is depicted as a refracted light beam 46 that will repeatedly change its polarization characteristics from linearly polarized to elliptically polarized to circularly polarized to elliptically polarized and back to linearly polarized as it passes through the stress field and will generate fluorescent light 48 that will have a polarization dependent component at each point along the light beam 42 in the side wall of the glass container 30. The polarization of the fluorescent light 48 orthogonal to the laser beam 46 will be primarily linear polarized, but with a fixed intensity variation attributed to the stress experienced while entering the glass plus a range of other things, including the color of the glass.

The emitted linearly polarized fluorescent light 48 from the laser beam 46 is affected by the stress induced retardance along the exit path such that the fluorescent light 48 represents just one specific ray from near the center of the container wall thickness. It is important to note that the light beam 46 will generate fluorescent light along its length, and that line of fluorescent light, of which the fluorescent light 48 represents one ray, will exit the glass container 30 through the outside wall 32, where it will constitute the line light to be imaged, of which the light beam 50 represents one ray.

A quarter wave plate 52 mounted at an appropriate angle is used to convert the elliptically polarized components of the light beam 50 into linearly polarized light to allow an evaluation of how much of the linearly polarized fluorescent light 48 became circularly or elliptically polarized. The orientation of the axis of the quarter wave plate 52 will be at an angle that is aligned with respect to the linearly polarized light radiating from the fluorescence along the light beam 46. A polarization rotator 54 is used to modulate the state of the polarization state of the now linearly polarized light beam 50 plus and minus 45 degrees with respect to the axis of the quarter wave plate 52, which itself is also at an angle of 45 degrees with respect to the linearly polarized light radiating from the fluorescence along the light beam 46. The polarization rotator 54 is a ferroelectric liquid crystal ("FLC") element that is driven by alternating positive and negative voltages from a rotator drive 56.

The thusly modulated linearly polarized light beam 50 then passes through a long pass filter 58 that passes fluorescent light (and preferably does not pass light at the frequency of the linearly polarized light beam 42), with the fluorescent portion of the linearly polarized light beam 50 being viewed by a CCD camera 60. Alternately, a bandpass filter or a notch filter could be used instead of the long pass filter 58. Alternating images are produced by the CCD camera 60 with the alternating positive and negative voltages produced by the rotator drive 56 driving the polarization rotator 54. These alternating images are acquired from the CCD camera 60 by an image acquisition module 62, and are schematically depicted as a first image 64 that is produced when the rotator drive 56 supplies a positive voltage to the polarization rotator 54, and a second image 66 that is produced when the rotator drive 56 supplies a negative voltage to the polarization rotator 54. (Those skilled in the art will appreciate that the alternating images produced are of different polarization analysis states, and the alternating could instead be produced by other apparatus, such as, for example, by using two sensors with a polarizing beam splitter.)

These two images 64 and 66 are processed by subtracting the second image 66 from the first image 64 and dividing by the sum of the two images 64 and 66, with a normalized difference image 68 being produced. By processing the normalized difference image 68 in an image analysis module 70, a retardance curve and a stress parabola similar to those illustrated in FIG. 2 may be derived, and by processing this data the thickness of each of the stress layers in the wall of a glass container as well as the thickness of the wall itself may also be derived. This analysis will be discussed in more detail in conjunction with FIG. 13.

It should be noted that in order to obtain the thickness of the wall itself and/or the thickness of each of the stress layers in the wall of a glass container, it is not necessary to use the normalized difference image 68. Instead, by processing the data from either of the images 64 and 66, the thickness of the wall itself and the thickness of each of the stress layers in the wall of a glass container may be derived without use of the normalized difference image 68. Further, if only the thickness of the wall itself and the thickness of each of the stress layers in the wall are being measured, the apparatus shown in FIG. 3 would not need the quarter wave plate 52 or the polarization rotator 54. Instead, the CCD camera 60 would acquire a single image through the long pass filter 58 of the polarized components of the light beam 50 emitted from the glass container 30.

Figure 4:
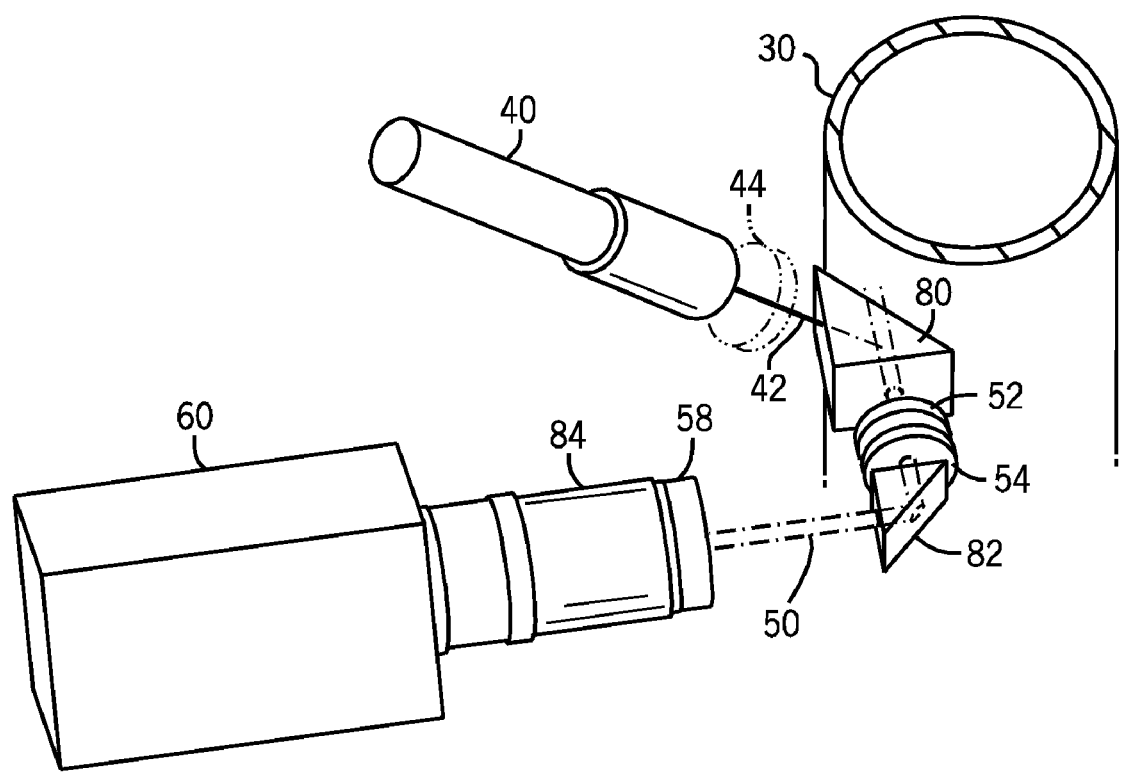
FIG. 4 is an isometric view of the essential components of the glass thickness measurement system of the present invention illustrated in FIG. 3 being used to evaluate the wall of a glass container, with an optional prism being used to make the apparatus more compact.
Figure 5:
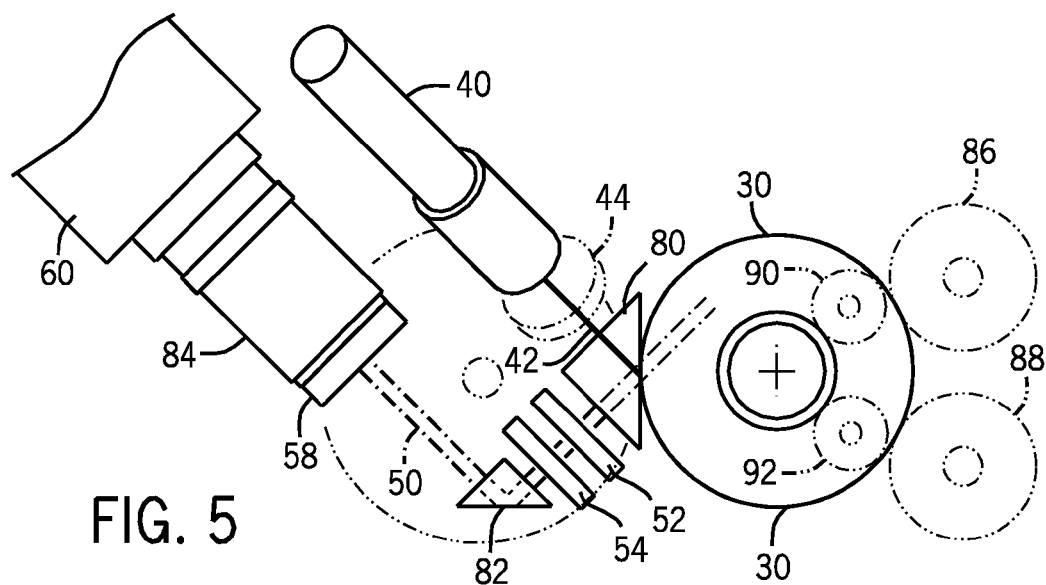
FIG. 5 is a plan view of the apparatus and glass container illustrated in FIG. 4 from the top thereof, also schematically showing apparatus used to rotate the glass container.
Figure 6:
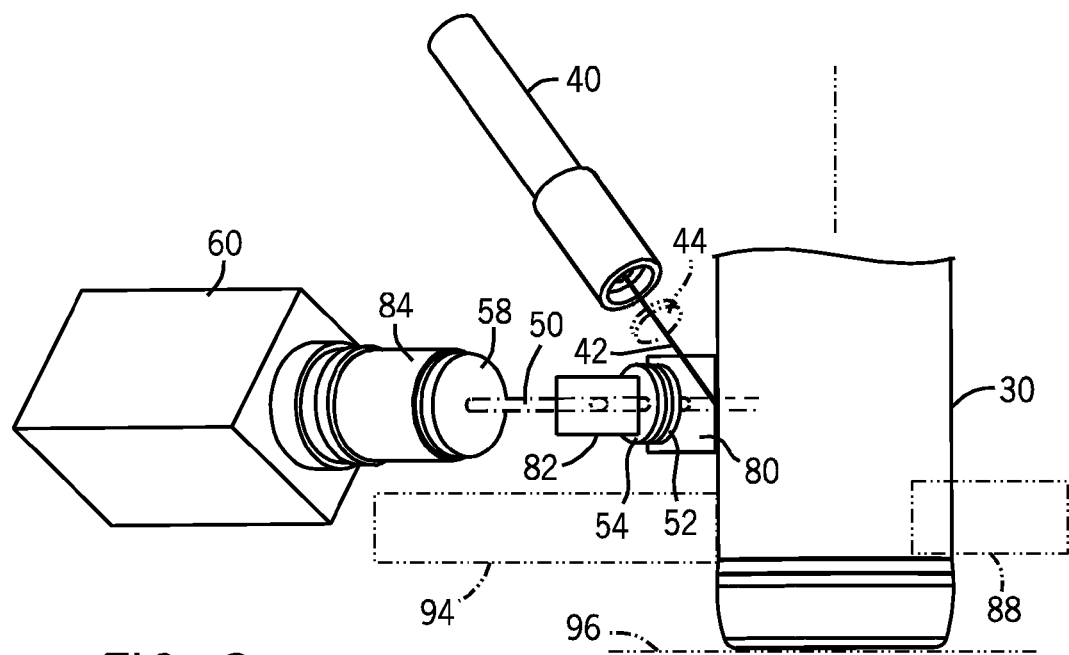
FIG. 6 is an elevation view of the apparatus and glass container illustrated in FIGS. 4 and 5 from the side thereof in the horizontal plane of the entry of the light beam into the side wall of the glass container.
Figure 7:
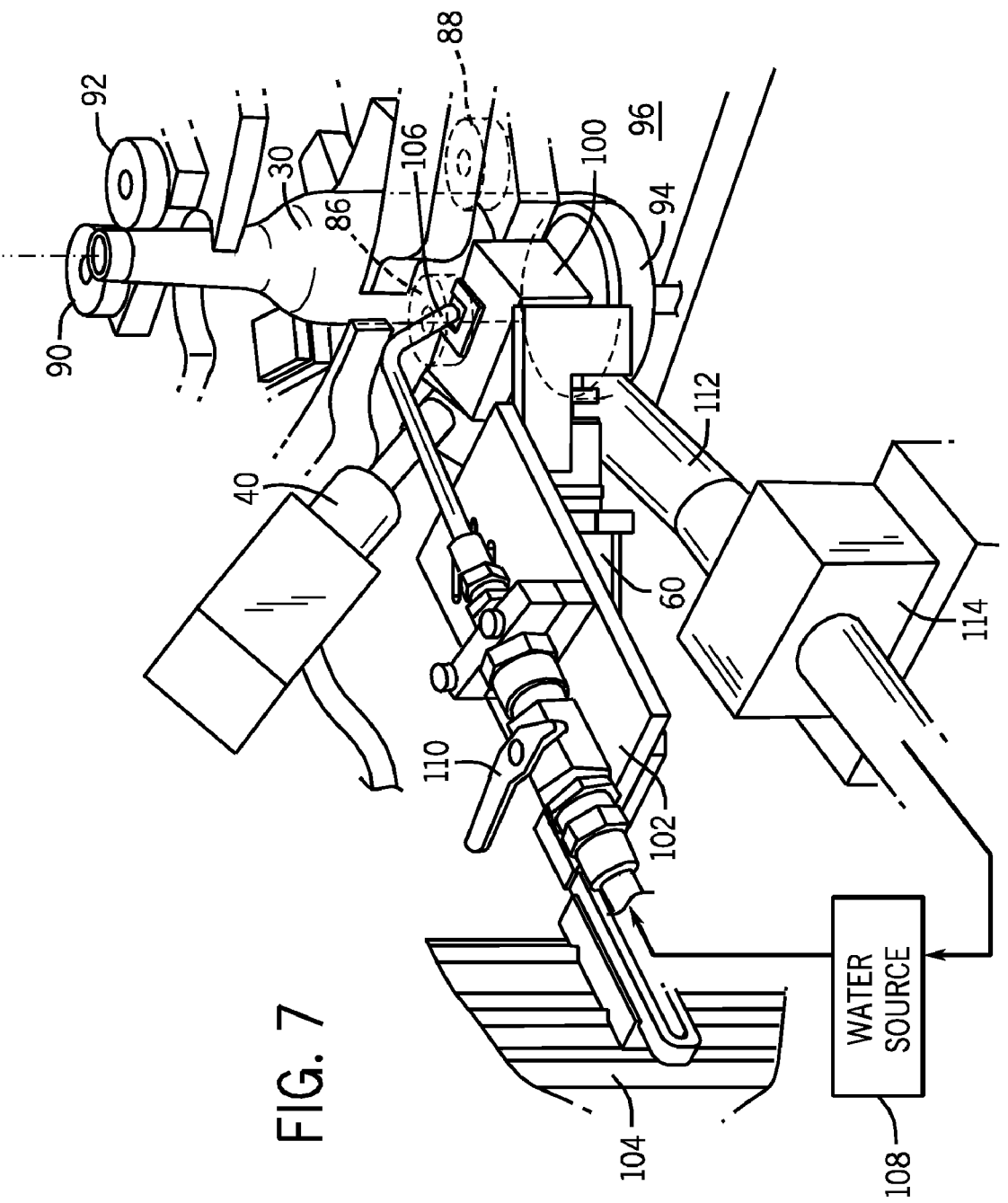
FIG. 7 is an isometric view of the apparatus and glass container illustrated in FIGS. 4 through 6 located in mounting apparatus used to support the various components adjacent a starwheel glass container apparatus, also showing a coupling fluid distribution system used to provide fluid coupling of the light into and out of the glass container.

Referring next to FIGS. 4 through 6, the system that is schematically illustrated in FIG. 3 with respect to the glass container 30 is illustrated in an exemplary embodiment omitting for clarity a housing member that will be used to maintain the relative locations of the various components and their optical paths respectively fixed in their preferred locations (this housing member which is unseen in FIGS. 4 through 6 is depicted in FIG. 7 as a component identified by the reference numeral 100) Wherever possible, the reference numbers used in FIG. 3 are also used in FIGS. 4 through 6.

It should be noted that the glass thickness measurement system and method of the present invention shown in FIGS. 4 through 6 is geometrically designed to use water (which has an index of refraction close to the that of glass) as a coupling fluid to couple light into and out of the glass container 30, while the alternate use of air as coupling fluid would necessitate different geometry to optimize the coupling of light into and out of the glass container 30. Thus, those skilled in the art will appreciate that the optimal angles of entry into and exit from the glass container 30 will be different for different coupling fluids.

The light beam used for the analysis is generated by the laser light source 40. In the exemplary embodiment, the laser light source 40 may be a diode laser in any of a variety of different colors, including, for example, green, blue, and red. The particular color of the laser light to be used may be selected based upon the characteristics of the glass container to be inspected. For example, a red laser is believed to be best with amber glass containers since amber glass absorbs green and blue light. A green laser is believed to be best for flint colorless glass containers, and a blue laser is believed to be best with bluish color glass containers. An exemplary setup for use in analyzing clear colorless glass containers may use a green laser.

The laser light selection criteria used should include the fact that fluorescent light has a longer wavelength than the light that is used to create it. Accordingly, the selection of the laser light source 40 should be made to make it easy to observe the fluorescent light generated in the wall of the glass container 30. Thus, deep red will be produced from a red laser beam, green to red will be produced from a blue laser beam, and yellow to deep red will be produced from a green laser beam. The excitation wavelength may also be chosen by the magnitude of the nearly linear polarization in the emitted fluorescence.

The laser light source 40 generates a linearly polarized laser light beam 42 of an appropriately selected wavelength that will be coupled into the side wall of the glass container 30. The linearly polarized light beam 42 is oriented with a polarization direction that is selected to produce an optimal (the largest possible magnitude) fluorescent signal intensity of the light beam 50 exiting the side wall of the glass container 30. This polarization direction will be in a plane that is parallel to a plane that is orthogonal to the axis of fluorescent light exiting the side wall of the glass container 30. While in the exemplary embodiment the half wave plate 44 shown in phantom lines may be used to rotate the polarization of the linearly polarized light beam 42 to the desired orientation, it may be easier to mount the laser light source 40 such that it may be rotated to rotate the polarization of the linearly polarized light beam 42 to the desired orientation.

The linearly polarized light beam 42 is coupled into the glass container 30 in the exemplary embodiment illustrated in FIGS. 4 though 6 using a right angle isosceles coupling prism 80 that is oriented with its hypotenuse located tangentially (and with its triangular surfaces in horizontal planes) with respect to the side wall of the glass container. As mentioned above, the embodiment illustrated in FIGS. 4 through 6 is geometrically designed to use water as the coupling fluid between the coupling prism 80 and the outside wall of the glass container 30. The laser light source 40 is mounted such that the linearly polarized light beam 42 will enter one of the shorter sides of the coupling prism 80 at a downwardly oriented angle of approximately 45 degrees from a horizontal plane (which plane is orthogonal to the axis of the glass container 30).

For the water-coupled embodiment being discussed, this will orient the linearly polarized light beam 42 such that it enters the side wall of the glass container 30 at an angle of approximately 45 degrees from the normal to the surface of the glass container 30 at the point of entry when viewed from directly above (this angle being in the horizontal plane orthogonal to the axis of the glass container 30), and at a 45 degree angle from the horizontal plane orthogonal to the axis of the glass container 30. This approximate angle of entry is selected to maximize the linear polarization and signal.

This results in a compound angle at the surface of the glass container 30 of 60 degrees from the normal to the surface. Since the index of refraction for water is 1.333 and the approximate index of refraction for the material of the glass container 30 is 1.51, the resulting angle in the wall of the glass container 30 will be approximately 40.51 degrees from the normal. Due to the curvature of the glass container 30, the relative positioning of the glass container 30, and variations in the glass container 30 due to production tolerances, this angle will vary slightly.

Thus, the light beam 46 is oriented inside the glass of the side wall of the glass container 30 in order to provide optimum signal levels. In this configuration, the axial stress is entirely affecting the vertical component of the 45 degree angle polarization, and only a portion of the hoop stress, combined with the nearly zero radial stress, are affecting the horizontal component of the 45 degree polarization. At other angles of orientation of the fluorescent light 48 from the fluorescence from the light beam 46, contribution by axial and hoop stress will vary according to the component of the stress field that the polarized light beam 42 crosses.

This geometric relationship is selected for a water-coupled embodiment to put the fluorescence from the light beam 46 in the focus plane of the CCD camera 60 and the right angle (orthogonal) relationship between the exciting linearly polarized light beam 42 and the viewing angle maximizes the linear polarization and signal, and also since the use of a smaller angle results in a small signal.

The location from which the fluorescent light generated from the light beam 42 inside the side wall of the glass container 30 is observed is orthogonal to the other of the shorter sides of the coupling prism 80, with the light beam 50 being oriented in the horizontal plane at an angle of approximately 45 degrees from the normal to the surface of the glass container 30. The light beam 50 is thus the result of the fluorescence whose linear polarization component is at 45 degrees to horizontal, and has been affected by the stress field along the path from the fluorescence source along the light beam 46 to its exit from the glass container 30.

The light beam 50 then passes through the quarter wave plate 52 and the polarization rotator 54. For purposes of convenience in mounting the various components of the glass thickness measurement apparatus of the present invention in a compact configuration, a bending prism 82 is used to bend the light beam 50 at a 90 degree angle. The bending prism 82 is also a right angle isosceles prism.

After passing through the quarter wave plate 52 and the polarization rotator 54, the light beam 50 is bent in the bending prism 82, and then passes through the long pass filter 58, which is mounted on a lens 84 of the CCD camera 60. The orientation of the axis of the quarter wave plate 52 would be at an angle that is aligned with respect to the linearly polarized light from the fluorescence within the glass container 30, ignoring the presence of the bending prism 82 and assuming that the quarter wave plate 52 was mounted parallel to the other of the shorter sides of the coupling prism 80.

The quarter wave plate 52 may be selected by doing a fluorimeter plot of intensity as it varies by wavelength, and using the wavelength of the highest intensity point of the plot to select the appropriate the quarter wave plate 52. For example, if the highest intensity point is at 700 nanometers, a 175 nanometer quarter wave plate 52 would be selected. The appropriate polarization rotator 54 may be selected in similar fashion.

The lens 84 may have an aperture that is wide open to allow more light to reach the CCD camera 60, since virtually no depth of focus is necessary to view the light beam 42 as it passes through the side wall of the glass container 30 in a plane that extends downwardly at approximately 45 degrees. The fluorescent light that generates the light beam 50 extends orthogonally out of that focal plane and may thus be captured by the CCD camera 60. Thus the line of view captured by the CCD camera 60 is at 45 degrees from a plane tangential to the side wall of the glass container 30, and in the horizontal plane.

Also shown in FIGS. 5 and 6 in phantom lines is apparatus for rotating the glass container 30 in order to allow the apparatus of the present invention to measure the stress in the side wall of the glass container 30 as well as its thickness at a plurality of angular positions as the glass container 30 is rotated. One side of the glass container 30 is supported for rotation near its bottom by a pair of rollers 86 and 88 and near its top by a pair of rollers 90 and 92. A drive roller 94 is used to rotate the glass container 30, which is supported on a deadplate 96. In the exemplary embodiment, the stresses and the thickness of the side wall of the glass container 30 will be evaluated at approximately 20 degree angular increments, which has been found to be a sufficient sampling in order to fully evaluate the stresses and the thickness of the side wall of the glass container 30.

Prior to further elaborating on the implementation of the water-coupled embodiment, the geometry for an air-coupled embodiment may first be discussed. At present, it is believed that the optimal geometry for an air-coupled embodiment would orient the linearly polarized light beam 42 such that it enters the side wall of the glass container 30 at an angle of approximately 60 degrees from the normal to the surface of the glass container 30 at the point of entry when viewed from directly above (this angle being in the horizontal plane orthogonal to the axis of the glass container 30), and at a 45 degree angle from the horizontal plane orthogonal to the axis of the glass container 30. This approximate angle is selected for an air-coupled embodiment to maximize the linear polarization and signal.

This would result in a compound angle at the surface of the glass container 30 of 69.29 degrees from the normal to the surface. Since the index of refraction for air is 1.0 and the approximate index of refraction for the material of the glass container 30 is 1.51, the resulting angle in the wall of the glass container 30 will be approximately 38.278 degrees from the normal. Due to the curvature of the glass container 30, the relative positioning of the glass container 30, and variations in the glass container 30 due to production tolerances, this angle would vary slightly.

The location from which the fluorescent light generated from the light beam 42 inside the side wall of the glass container 30 is air-coupled out of the glass container 30 would provide the light beam 50 at an orientation in the horizontal plane at an angle of approximately 60 degrees from the normal to the surface of the glass container 30. These approximate angles of entry into and exit from the glass container are selected to maximize the signal detected (the light beam 50 emitted from the glass container 30).

In general, and for a wide variety of potential coupling fluids, the preferred orientations of the glass thickness measurement system and method of the present invention appear to be angles of between approximately 40 degrees and approximately seventy from the normal to the surface of the glass container 30 at the point of entry when viewed from directly above, with a 45 degree angle from the horizontal plane orthogonal to the axis of the glass container 30.

Referring now to FIG. 7, the installation of the apparatus of FIGS. 4 through 6 into a production environment using water as a coupling fluid is illustrated. The laser light source 40 and the CCD camera 60 are shown mounted into a machine head housing 100. The coupling prism 80, the bending prism 82, the quarter wave plate 52, and the polarization rotator 54 are mounted inside the machine head housing 100 in the orientation in which they are shown in FIGS. 4 through 6. The machine head housing 100 is mounted on a support arm, indicated generally by the reference numeral 102, which in turn is mounted on a support column 104.

As mentioned above, fluid coupling is used to couple the light between the coupling prism 80 and the side wall of the glass container 30. In this exemplary embodiment, water is used as the coupling fluid, since it has an index of refraction that is close to that of glass. The water is delivered to a point just above the interface between the coupling prism 80 and the side wall of the glass container 30 by a nozzle 106. The water is delivered from a fluid source 108 such as a pump through a valve 110 to the nozzle 106.

The water is collected from under the machine head housing 100 at the underside of the interface between the coupling prism 80 and the side wall of the glass container 30 by a vacuum tube 112. A fluid vacuum 114 is connected to the vacuum tube 112 to collect the water, and returns it to the fluid source 108 for reuse. If desired, a filter may be inserted between the fluid vacuum 114 and the fluid source 108 to clean impurities from the water prior to supplying it to the fluid source 108.

Figure 8:
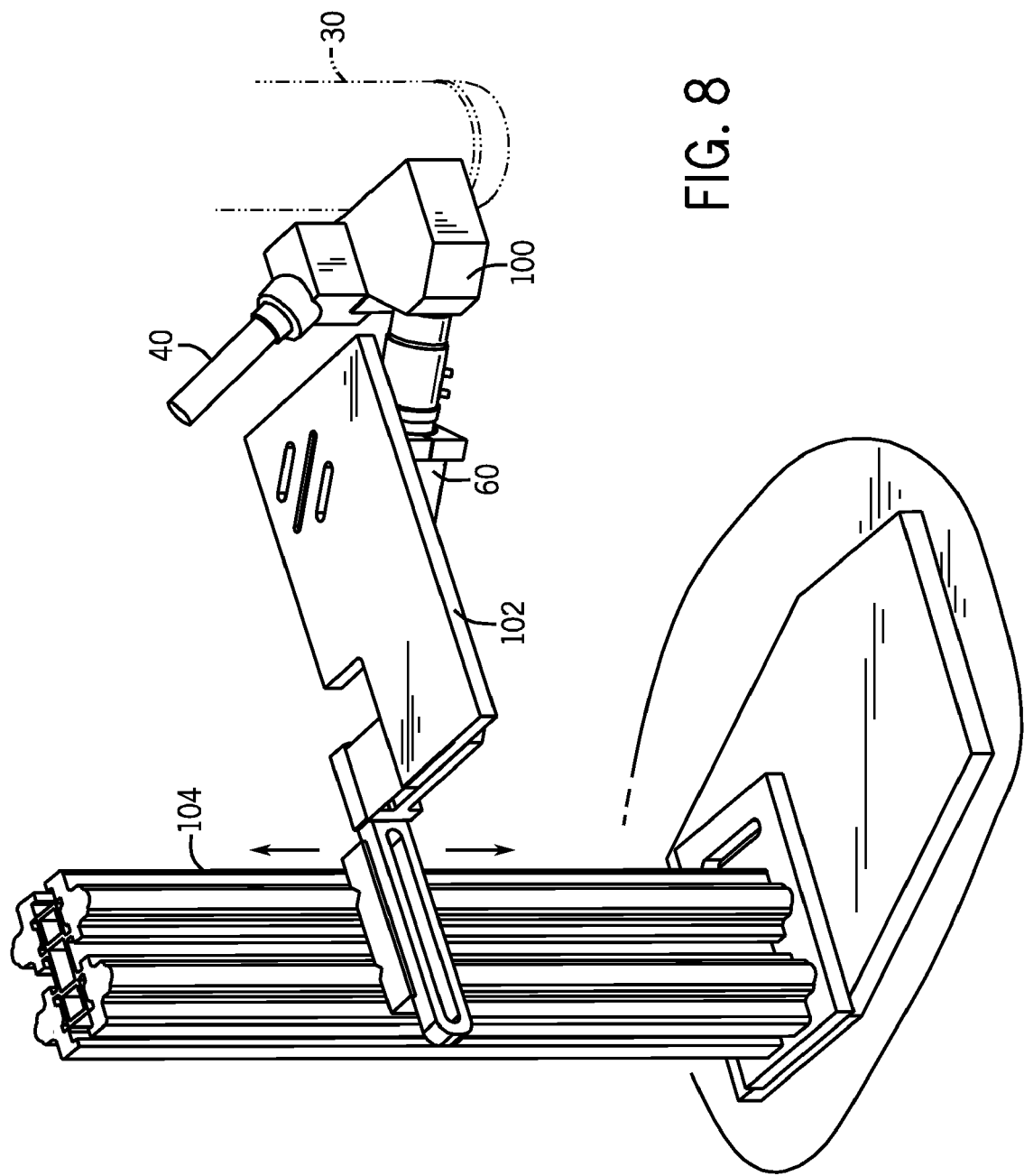
FIG. 8 is an isometric view of the apparatus illustrated in FIG. 7, showing an adjustable support mechanism for the apparatus.
Figure 9:
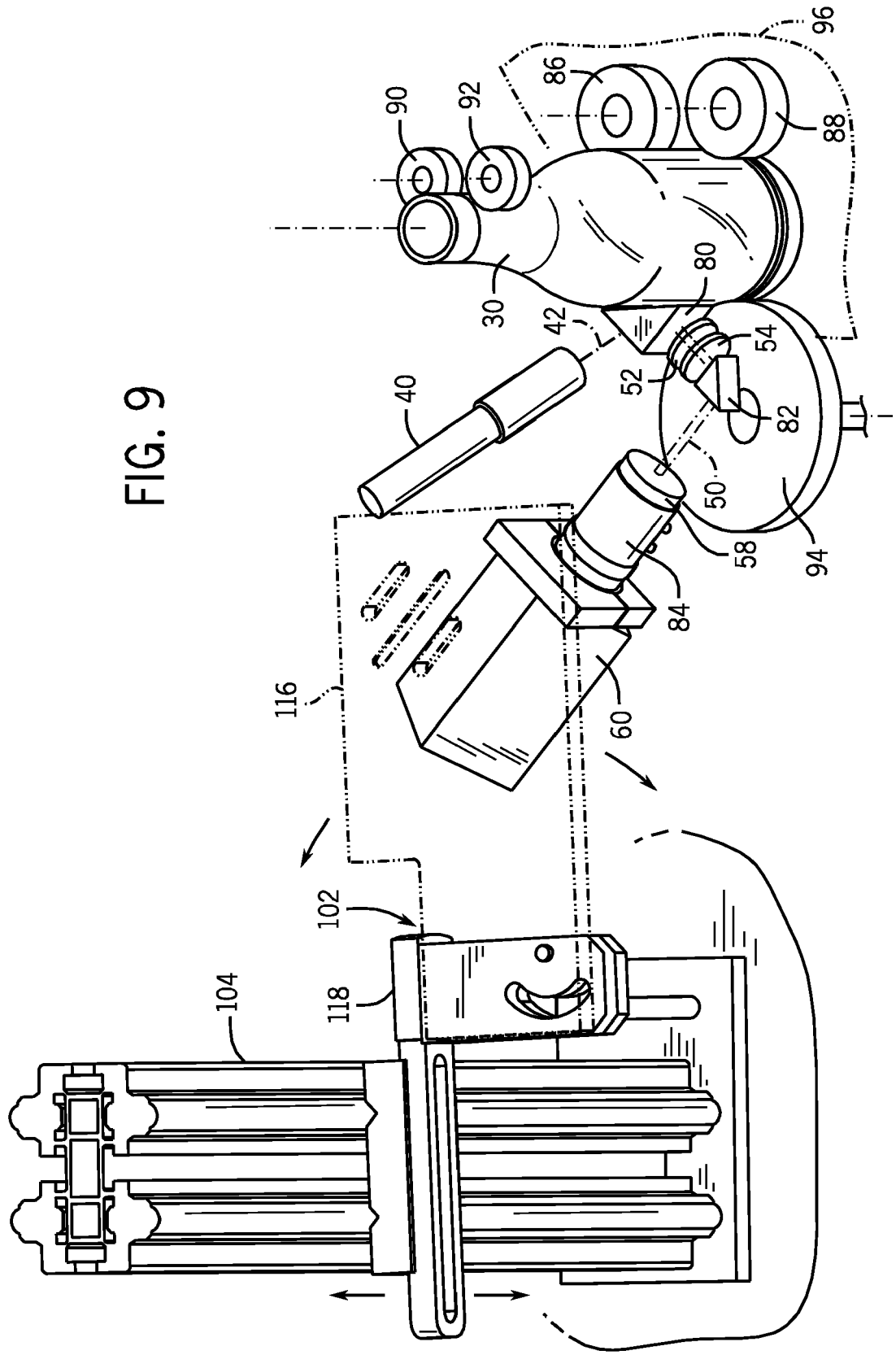
FIG. 9 is a is an isometric view of the apparatus illustrated in FIG. 8, with the various housing elements removed for clarity, together with a glass container being tested.

Referring briefly to FIGS. 8 and 9, the apparatus of the present invention is shown as it is mounted on the underside of the support arm 102. Referring specifically to FIG. 9, it may be seen that the support arm 102 may be of two-piece construction, thereby allowing for another degree of adjustment. A distal portion 116 of the support arm 102 is pivotally mounted on a proximal portion 118 of the support arm 102. This capability for adjustment, together with the ability to adjust the height of the support arm 102 on the support column 104, allows for the apparatus of the present invention to be adjusted to accommodate virtually any manufacturing line configuration.

Figure 10:
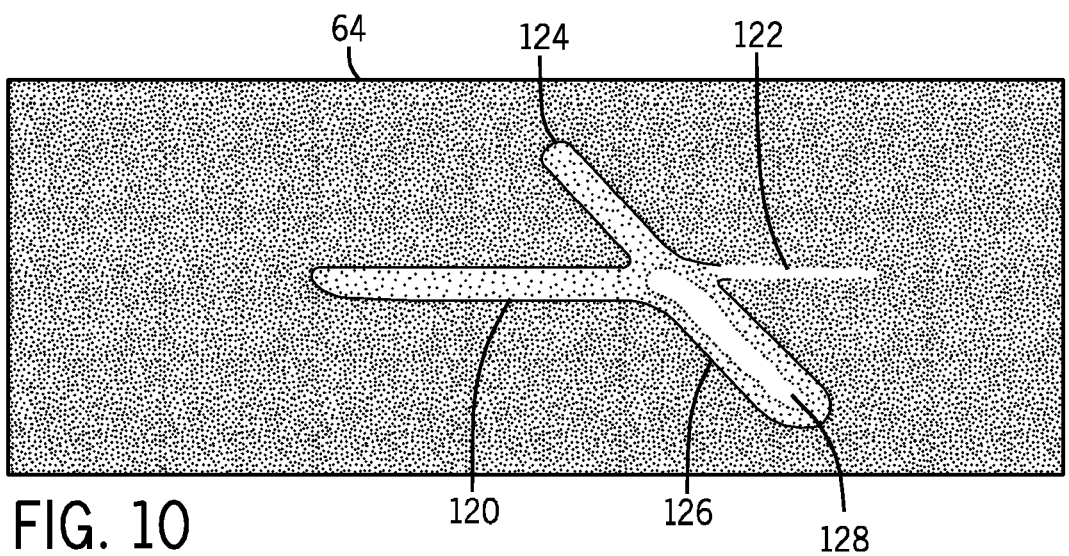
FIG. 10 is a first image taking by the camera at a first of the two alternating images having a first polar rotation.
Figure 11:
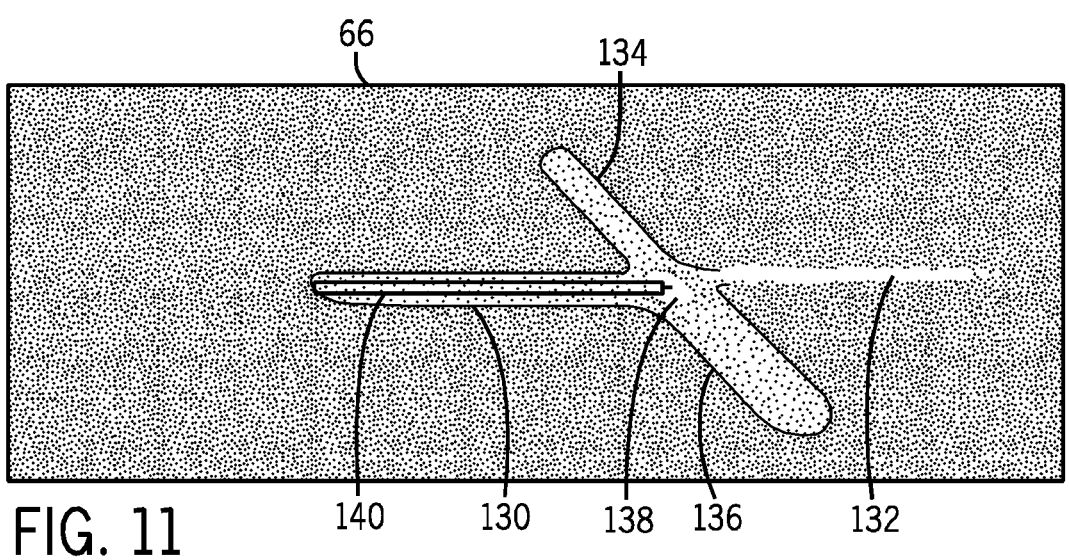
FIG. 11 is a second image taking by the camera at a second of the two alternating images having a second polar rotation orthogonal to the first polar rotation.

As mentioned above in conjunction with FIG. 3, two alternating images 64 and 66 are captured by the CCD camera 60. Exemplary such images 64 and 66 are respectively shown in FIGS. 10 and 11. The first image 64 shown in FIG. 10 is produced when the rotator drive 56 supplies a positive voltage to the polarization rotator 54, and the second image 66 shown in FIG. 11 is produced when the rotator drive 56 supplies a negative voltage to the polarization rotator 54.

Referring to the first image 64, an image that resembles a cross laying sideways with the crossbar of the cross being rotated counterclockwise from an orthogonal position is visible. The lower portion of the leg of the cross 120 extends from left to right, with the upper portion of leg of the cross 122 extending further to the right of the lower portion of the cross. A first side of the crossbar 124 extends from the intersection of the lower portion of the leg of the cross 120 and the upper portion of the leg of the cross 122 upwardly and leftwardly, and a second side of the crossbar 126 extends from the intersection of the lower portion of the leg of the cross 120 and the upper portion of the leg of the cross 122 downwardly and rightwardly. At the intersection of the leg of the cross and the crossbar of the cross is an intersection point of the cross 128.

The horizontal lower portion of the leg of the cross 120 is the fluorescent portion of the modulated linearly polarized light beam 50 that shows the fluorescence from the light beam 46 (shown in FIG. 3) inside the side wall of the glass container 30, which terminates in the bright spot at the intersection point of the cross 128 which is the inner wall of the glass container 30. The first side of the crossbar 124 is the reflection of the light beam 42 from the inner wall of the glass container 30, and the second side of the crossbar 126 from the intersection point of the cross 128 is the light beam 42 hitting the inner wall of the glass container 30 and being reflected downwardly into the glass of the side wall of the glass container 30 and produces fluorescent light along that path. The upper portion of the leg of the cross 122 is a reflection of the downwardly reflected light beam 46 in the glass represented by the second side of the crossbar 126.

Referring now to the second image 66, a similar cross-shaped image laying sideways with its crossbar being rotated counterclockwise from an orthogonal position is visible. The horizontal lower portion of the leg of the cross 130 extends from left to right, with the upper portion of leg of the cross 132 extending further to the right of the lower portion of the cross. A first side of the crossbar 134 extends from the intersection of the lower portion of the leg of the cross 130 and the upper portion of the leg of the cross 132 upwardly and leftwardly, and a second side of the crossbar 136 extends from the intersection of the lower portion of the leg of the cross 130 and the upper portion of the leg of the cross 132 downwardly and rightwardly. At the intersection of the leg of the cross and the crossbar of the cross is an intersection point of the cross 138.

As is the case in the first image 64, the horizontal lower portion of the leg of the cross 130 is the fluorescent portion of the modulated linearly polarized light beam 50 that shows fluorescence from the light beam 46 inside the side wall of the glass container 30, which terminates in the bright spot at the intersection point of the cross 138 which is the inner wall of the glass container 30. The first side of the crossbar 134 is the reflection of the light beam 46 from the inner wall of the glass container 30, and the second side of the crossbar 136 from the intersection point of the cross 138 is the light beam 42 hitting the inner wall of the glass container 30 and being reflected downwardly in the glass of the side wall of the glass container 30 and produces fluorescence along that path. The horizontal upper portion of the leg of the cross 132 is a reflection of the downwardly reflected light beam 46 in the glass represented by the second side of the crossbar 136. The location of the side wall of the glass container 30 is shown by a line 140 representing the thickness of the side wall of the glass container 30 that is drawn onto the second image 66 by the system to better identify the location of the side wall of the glass container 30. It should be noted that by processing the data from the second image 66, the thickness of the wall itself (shown by the line 140) and the thickness of each of the stress layers in the wall of a glass container may be derived. This information could also be derived from the first image 64 shown in FIG. 10.

Figure 12:
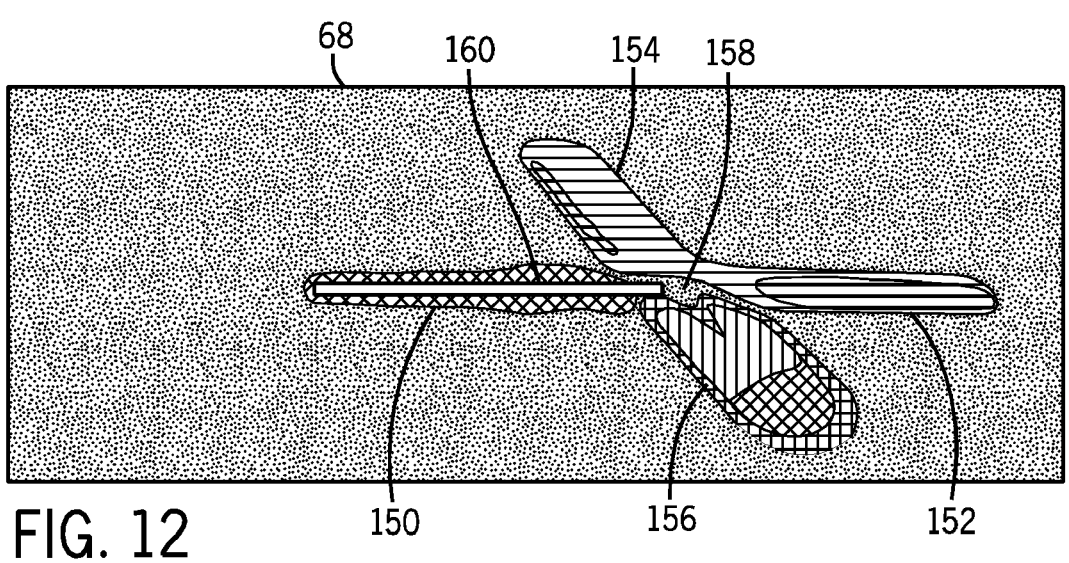
FIG. 12 is a normalized difference image taken by subtracting the second image illustrated in FIG. 11 from the first image illustrated in FIG. 10.

Referring next to FIG. 12, a normalized difference image 68 is shown that is generated by subtracting the second image 66 illustrated in FIG. 11 from the first image 64 illustrated in FIG. 10 and dividing by the sum of first image 64 and second image 66. The normalized difference image 68 shows a somewhat different cross-shaped image laying sideways with its crossbar being rotated counterclockwise from an orthogonal position is visible. The lower portion of the leg of the cross 150 extends from left to right, with the upper portion of leg of the cross 152 extending further to the right of the lower portion of the cross. A first side of the crossbar 154 extends from the intersection of the lower portion of the leg of the cross 150 and the upper portion of the leg of the cross 152 upwardly and leftwardly, and a second side of the crossbar 156 extends from the intersection of the lower portion of the leg of the cross 150 and the upper portion of the leg of the cross 152 downwardly and rightwardly. At the intersection of the leg of the cross and the crossbar of the cross is an intersection point of the cross 158.

Once again, the horizontal lower portion of the leg of the cross 150 is the fluorescent portion of the modulated linearly polarized light beam 50 that shows fluorescence from the light beam 46 inside the side wall of the glass container 30, which terminates in the bright spot at the intersection point of the cross 158 which is the inner wall of the glass container 30. The first side of the crossbar 154 is the reflection of the light beam 46 from the inner wall of the glass container 30, and the second side of the crossbar 156 from the intersection point of the cross 158 is the light beam 42 hitting the inner wall of the glass container 30 and being reflected downwardly in the glass of the side wall of the glass container 30. The upper portion of the leg of the cross 152 is a reflection of the downwardly reflected light beam 42 in the glass represented by the second side of the crossbar 156. The location of the side wall of the glass container 30 is shown by a line 160 representing the thickness of the side wall of the glass container 30 that is drawn onto the second image 66 by the system to better identify the location of the side wall of the glass container 30.

Figure 13:
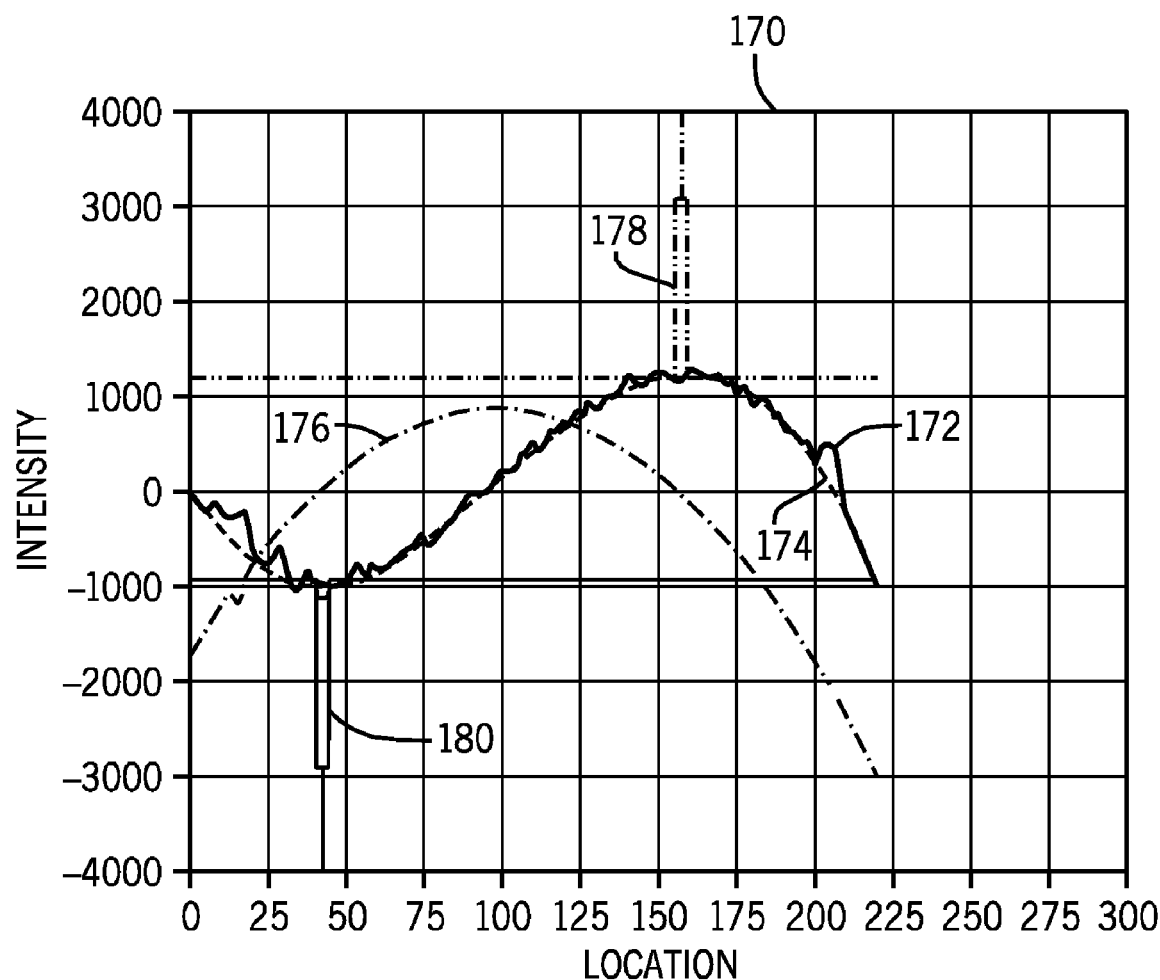
FIG. 13 is a display showing the line intensity of the portion of the normalized difference image shown in FIG. 12 plotted along the length of wall of the glass container, together with other information depicted as well in the display.

By processing the normalized difference image 68 of FIG. 12 in the image analysis module 70 (shown in FIG. 3), a glass stress display retardance curve 170 as shown in FIG. 13 may be generated. By plotting the intensity of the horizontal lower portion of the leg of the cross 150 of the normalized difference image 68 (shown in FIG. 12) along the line 160 representing the thickness of the side wall of the glass container 30 (also shown in FIG. 12), a jagged nominally S-shaped curve 172 maybe obtained. A polynomial best fit S-shaped curve 174 is generated from the rotated jagged nominally S-shaped curve 172, and represents the retardance curve of the side wall of the glass container 30.

The polynomial best fit S-shaped curve 174 is then differentiated by the system to produce a parabola 176 that is representative of the stress throughout the side wall of the glass container 30 at the location being tested. The system may also automatically determine the maximum and minimum locations in the polynomial best fit S-shaped curve 174, and these locations may be automatically displayed as a maximum trace 178 having a peak at the location determined to be the maximum of the polynomial best fit S-shaped curve 174 and as a minimum trace 180 having a peak at the location determined to be the minimum of the polynomial best fit S-shaped curve 174.

By further processing the data used to provide the glass stress display 170, the thickness of each of the stress layers in the wall of a glass container as well as the thickness of the wall itself may be derived. If desired, these calculations could also be shown on the glass stress display 170, although they are not so shown in FIG. 13. (As mentioned above, both the thickness of the wall and the thickness of each of the stress layers in the wall could also be derived from the first image 64 or the second image 66 instead.)

Figure 14:
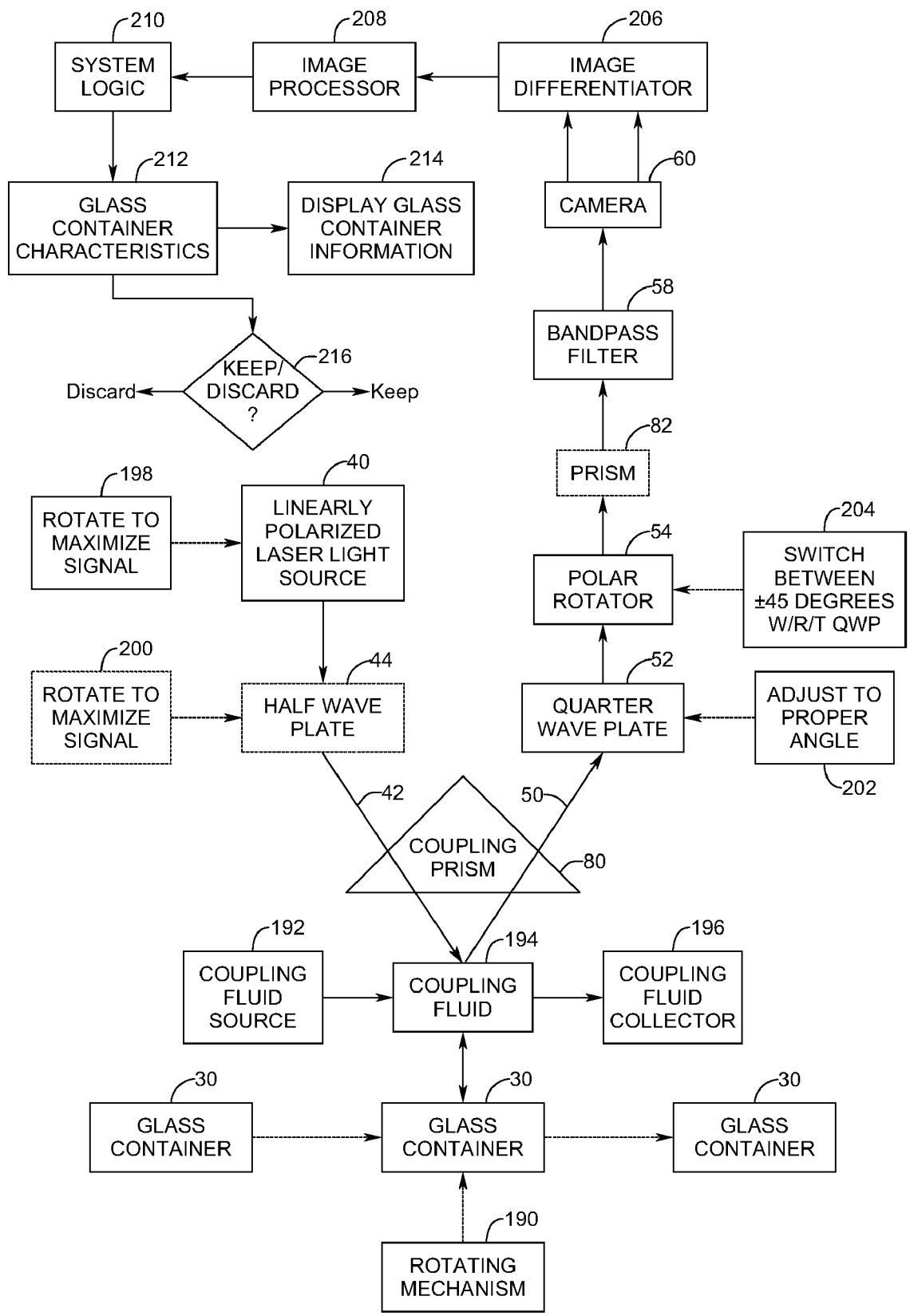
FIG. 14 is a flowchart showing the method used by the exemplary embodiment to measure glass stress and wall thickness.

Referring next to FIG. 14, the method practiced by the exemplary embodiment of the present invention is illustrated. A production line is used to successively bring each of a plurality of the glass containers 30 into position for inspection by the apparatus of the present invention. The glass container 30 in position for inspection is rotated by a rotating mechanism 190 so that the side wall of the glass container 30 may be inspected by the apparatus of the present invention at a plurality of angular locations. In the exemplary embodiment discussed herein, the glass container 30 inspection of the side walls of the glass container 30 will be taken approximately every 20 degrees, with the glass container 30 being rotated to take 18 successive readings that are each 20 degrees apart, thereby fully allowing the stress of the side wall of the glass container 30 and the wall thickness of the glass container 30 to be fully inspected.

A coupling fluid source 192, which may include the fluid source 108, 111, and the nozzle 106 (all of which are shown in FIG. 7), provides a coupling fluid 194, which as discussed above may be water, to a location between the coupling prism 80 and the side wall of the glass container 30. The coupling fluid is collected by a coupling fluid collector 196, which may include the vacuum tube 112 and the fluid vacuum 114 (which are also shown in FIG. 7) The coupling fluid may be filtered and returned to the coupling fluid source 192.

A linearly polarized light beam 42 is provided by the laser light source 40 and is coupled into the side wall of the glass container 30 through the coupling prism 80. The laser light source 40 may be mounted in a manner permitting it to be rotated as indicated by the reference numeral 198 to thereby rotate the polarization of the linearly polarized light beam 42 slightly to maximize the output signal from the system. Alternately, the half wave plate 44 may be placed between the laser light source 40 and the coupling prism 80, with the half wave plate 44 being rotated as indicated by the reference numeral 198 to thereby rotate the polarization of the linearly polarized light beam 42 slightly to maximize the output signal from the system.

The linearly polarized light beam 42 passes through the coupling prism 80 and the coupling fluid 194, and then enters into the side wall of the glass container 30, where it will generate fluorescent light have both linearly polarized and unpolarized components that will be affected by the stress state in the glass in its path to exit the side wall of the glass container 30 as the light beam 50. The light beam 50 is coupled from the side wall of the glass container 30 through the coupling prism 80. It passes through the quarter wave plate 52, which may be rotated as indicated by the reference numeral 202 to thereby optimize the conversion of the linearly polarized and elliptical components of the light beam 50 into linearly polarized light.

The linearly polarized light beam 50 is then passed through the polarization rotator 54, which is operated as indicated by the reference numeral 204 to produce alternating images having polar rotations each 45 degrees from the axis of the quarter wave plate 52. The alternating images from the linearly polarized light beam 50 may optionally be reoriented by the bending prism 82, following which they pass through the long pass filter 58 to filter out non-fluorescent frequencies.

The CCD camera 60 produces alternating images corresponding to the alternation of the polarization rotator 54, which alternating images are processed into a normalized difference image 68 in an image differentiator 206. The normalized difference image 68 is provided to an image processor 208 which processes the information from the normalized difference image 68 and provides the processed information to system logic 210. The system logic 210 provides as an output the characteristics 212 of the side wall of the glass container 30 that was inspected, which include the normalized difference image 68 which, together with other information, may be displayed in a display glass container information step 214. Following determination of the characteristics 212 of the side wall of the glass container 30 that was inspected at each of the angular positions for the glass container 30, a determination 216 may be made as to whether to keep or discard the glass container 30. Glass containers the glass container 30 not falling within appropriate ranges of wall thickness and stress may be discarded and recycled.

Figure 15:
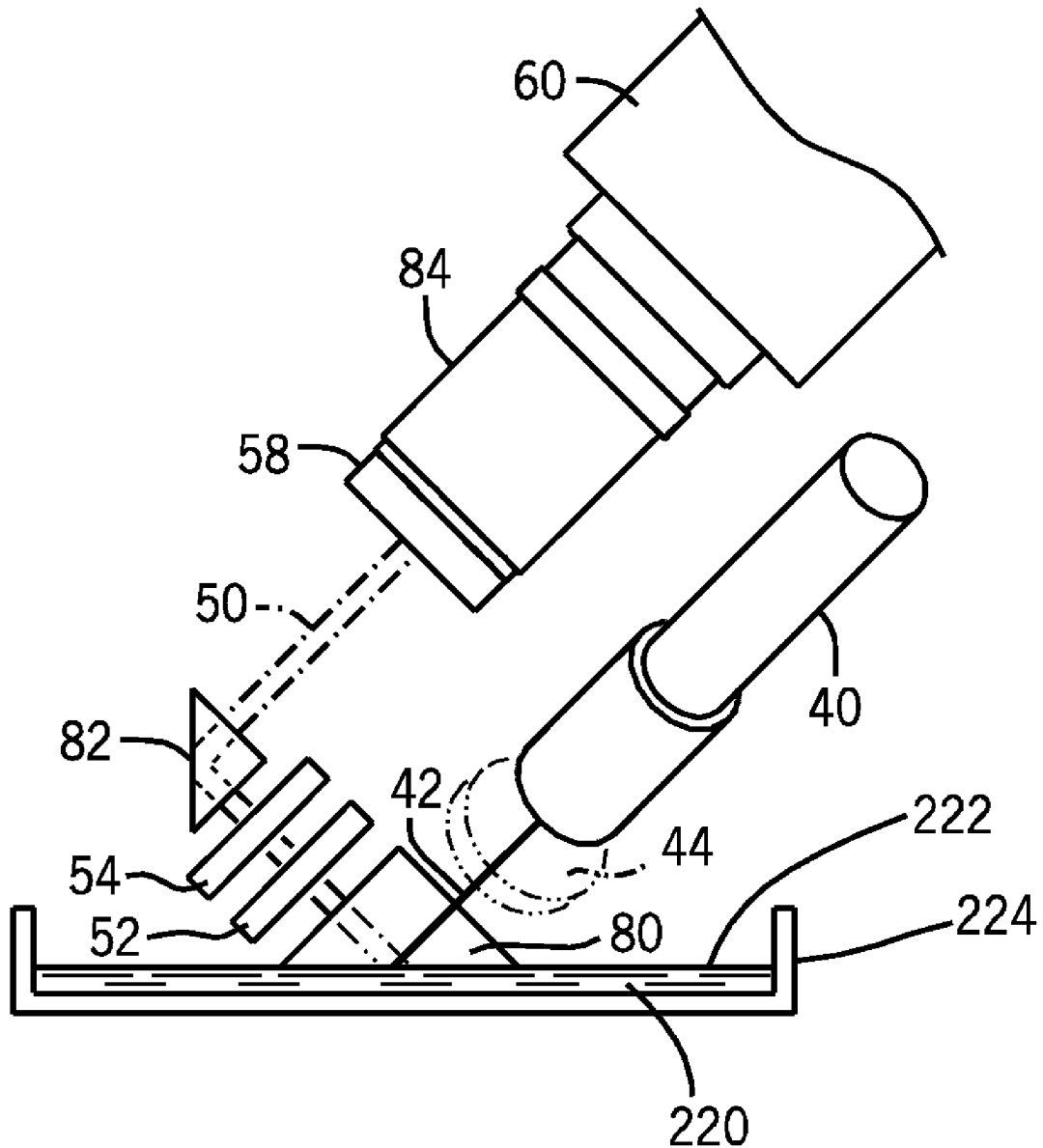
FIG. 15 is an isometric view of the essential components of the glass thickness measurement system of the present invention illustrated in FIG. 3 being used to evaluate the thickness of a segment of flat glass, with a coupling prism being used to make the apparatus more compact and a coupling fluid being located on the surface of the segment of flat glass to provide fluid coupling of the light into and out of the segment of flat glass.

Referring finally to FIG. 15, the use of the glass thickness measurement system of the present invention for measuring the stress in a segment of flat glass 220 is illustrated. The segment of flat glass 220 has a coupling fluid 222 which in the exemplary embodiment shown in FIG. 15 may be water, since water has an index of refraction that is close to that of glass than that of air. The segment of flat glass 220 may be located in a container 224 in order to confine a thin film of the coupling fluid 222 on the surface of the segment of flat glass 220.

Alternately, a coupling fluid supply and recycling system similar in function to the one illustrated in and discussed in conjunction with FIG. 7 above may be used to provide the coupling fluid 222 only in the area of the segment of flat glass 220 being measured may be utilized. Still another way using a liquid coupling agent would be to spray a thin film of the liquid coupling agent on the flat glass 220 immediately ahead of the movement thereto of the apparatus illustrated in FIG. 15. Further, (If a curved segment of glass is being evaluated, the spraying technique may prove to be particularly useful, since placing a thin film of coupling fluid on a curved segment of glass would be impractical.)

However, it may also be appreciated by those skilled in the art that the use of air coupling would be even more beneficial.

The optical system shown in and discussed in conjunction with FIGS. 4 through 6 above is shown and utilized in FIG. 15, with the coupling prism 80 having its hypotenuse located parallel to and close adjacent to the top side of the segment of flat glass 220 with a thin film of the coupling fluid 222 located between the coupling prism 80 and the top side of the segment of the segment of flat glass 220. The laser light source 40 is mounted such that the linearly polarized light beam 42 will enter one of the shorter sides of the coupling prism 80 at an angle of approximately 45 degrees from a plane parallel to the triangular sides of the coupling prism 80.

This results in the linearly polarized light beam 42 entering the top side of the segment of flat glass 220 at approximately a 40.51 degree angle with respect to the normal of the segment of flat glass 220 at the point of entry. Fluorescent light generated from the light beam 42 inside the glass of the segment of flat glass 220 is observed exits to the other of the shorter sides of the coupling prism 80. The light beam 50 has been affected by the stress field within the segment of flat glass 220.

The light beam 50 passes through the quarter wave plate 52 and the polarization rotator 54. For purposes of convenience in mounting the various components of the glass thickness measurement apparatus in a compact configuration, the bending prism 82 is used to bend the light beam 50 at a 90 degree angle. After passing through the quarter wave plate 52 and the polarization rotator 54, the light beam 50 is bent in the bending prism 82, and then passes through the long pass filter 58, which is mounted on a lens 84 of the CCD camera 60.

Thus, it will also be appreciated by those skilled in the art that, as is the case with the glass container 30 discussed above, if air coupling is used, the compound angle of entry of 69.29 degrees from the normal to the surface of the flat glass 220 would be maintained. This angle would be achieved by using angles of 45 and 60 degrees respectively in orthogonal planes normal to the surface of the flat glass 220 similarly to the example previously discussed with respect to the glass container 30. The angle of exit from the flat glass 220 would also be 60 degrees for air coupling. Curved glass would be evaluated in a similar manner with the same angles relative to the normal being used for water or air coupled operation.

It will thus be appreciated by those skilled in the art that the embodiment shown in FIG. 15 is illustrative of the use of the present invention to determine the stress contained within flat glass. Depending upon the size of the segment of flat glass 220, an X-Y scanning technique may be used to measure stress at each of a plurality of spaced-apart points in a linear progression in a first axis (the X direction), with the scanning apparatus then being moved in a second axis (the Y Direction) which is orthogonal to the first axis, at which point another scan may be done in the direction of the first axis, with this process being repeated until the entire segment of flat glass 220 has been evaluated.

It may therefore be appreciated from the above detailed description of the exemplary embodiments of the present invention that it teaches a glass thickness measurement system as well as a related method of measuring the stress in flat glass or curved glass segments. The glass thickness measurement system and method of the present invention are adaptable for large scale flat glass or curved glass segment manufacturing, and they are thus capable of high speed measurement of the stress in flat glass or curved glass segments. The glass thickness measurement system and method of the present invention also do not require that the flat glass or curved glass segments be immersed in liquid during the inspection process, thereby not increasing the handling of the flat glass or curved glass segments being inspected.

The glass thickness measurement system and method of the present invention produce highly accurate determinations of the stress in flat glass or curved glass segments. The glass thickness measurement system and method of the present invention are also capable of measuring the thickness of each of the stress layers in flat glass or curved glass segments. The glass thickness measurement system and method of the present invention are capable of measuring the wall thickness of the flat glass or curved glass segments. The glass thickness measurement system and method of the present invention are capable of quickly and accurately measuring both the stress in and the thickness of a plurality of positions in the flat glass or curved glass segments.

The glass thickness measurement system of the present invention is of a construction which is both durable and long lasting, and it should also require little or no maintenance to be provided by the user throughout its operating lifetime. The glass thickness measurement system of the present invention is also be of relatively inexpensive construction to enhance its market appeal and to thereby afford it the broadest possible market. Finally, the glass thickness measurement system and method of the present invention achieves all of the aforesaid advantages and objectives without incurring any substantial relative disadvantage.

Although the foregoing description of the glass thickness measurement system and method of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the glass thickness measurement system and method of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the glass thickness measurement system and method of the present invention as determined by the appended claims when interpreted in accordance with the breadth to which they are fairly, legally, and equitably entitled.

What is claimed is:

1. An apparatus for measuring the thickness of a segment of glass, comprising:
    a light beam source that generates a light beam;
    light beam coupling apparatus for directing said light beam at the side of a segment of glass at an angle facilitating entry of said light beam into and through the side of the segment of glass, said light beam causing fluorescent light to be emitted within the segment of glass in response to said light beam within the side of the segment of glass;
    fluorescent light coupling apparatus for coupling a portion of said fluorescent light emitted in response to said light beam within the segment of glass outwardly from the side of the segment of glass; and
    fluorescent light processing and analysis apparatus that processes the fluorescent light exiting the side of the segment of glass and determines the thickness of the segment of glass from the processed fluorescent light exiting the side of the segment of glass.

2. As apparatus as defined in claim 1, wherein said light beam source comprises:
    a laser that produces a light beam which is linearly polarized.

3. As apparatus as defined in claim 2, wherein said light beam source additionally comprises:
    polarization adjustment apparatus which is adjustable to rotate the polarization of said linearly polarized light beam to a desired orientation that will produce an the largest possible fluorescent light emitted in response to said light beam within the segment of glass.

4. As apparatus as defined in claim 3, wherein said polarization adjustment apparatus comprises:
    laser mounting apparatus for securing said laser in position, wherein said laser mounting apparatus selectively allows said laser to be rotated to thereby rotate the polarization of said linearly polarized light beam to a desired orientation.

5. As apparatus as defined in claim 3, wherein said polarization adjustment apparatus comprises:
    a half wave plate located intermediate said laser and said light beam coupling apparatus, said half wave plate being selectively rotatable to thereby rotate the polarization of said linearly polarized light beam to a desired orientation.

6. As apparatus as defined in claim 1, wherein said light beam coupling apparatus and said fluorescent light coupling apparatus collectively comprise:
    an optical coupling member for location adjacent the side of the segment of glass, said light beam being directed onto said optical coupling member whereupon said optical coupling member directs said light beam into the side of the segment of glass, said fluorescent light emitted from the side of the segment of glass being collected by said optical coupling member whereupon said optical coupling member directs the emitted fluorescent light into fluorescent light processing and analysis apparatus.

7. As apparatus as defined in claim 6, wherein said optical coupling member comprises:
    a coupling prism.

8. As apparatus as defined in claim 6, wherein said optical coupling member is arranged and configured to couple said light beam into the segment of glass and to couple said emitted fluorescent light out of said segment of glass using air as a coupling medium.

9. As apparatus as defined in claim 8, wherein said optical coupling member is arranged and configured to couple said light beam into the segment of glass at a compound angle that comprises an angle of between approximately 40 degrees and approximately 70 degrees from a plane normal to the surface of the glass container at the point of entry, and at an approximately 45 degree angle out of said plane.

10. As apparatus as defined in claim 9, wherein said optical coupling member is arranged and configured to couple said light beam into the segment of glass at a compound angle that comprises an angle of between approximately 60 degrees from said plane normal to the surface of the glass container at the point of entry, and at an approximately 45 degree angle out of said plane.

11. As apparatus as defined in claim 6, additionally comprising:
    apparatus for directing a stream of liquid coupling fluid intermediate said optical coupling member and the segment of glass to optically couple said light beam into the segment of glass and to couple said emitted fluorescent light out of the segment of glass;
    wherein said optical coupling member is arranged and configured to facilitate the coupling of said light beam into the segment of glass and to facilitate the coupling of said emitted fluorescent light out of the segment of glass.

12. As apparatus as defined in claim 11, wherein said optical coupling member is arranged and configured to couple said light beam into the segment of glass at a compound angle that comprises an angle of between approximately 40 degrees and approximately 70 degrees from a plane normal to the surface of the segment of glass at the point of entry, and at an approximately 45 degree angle out of said plane.

13. As apparatus as defined in claim 12, wherein said optical coupling member is arranged and configured to couple said light beam into the segment of glass at a compound angle that comprises an angle of between approximately 45 degrees from the normal to the surface of the segment of glass at the point of entry in said plane orthogonal to an axis of the glass container, and at an approximately 45 degree angle from said plane.

14. As apparatus as defined in claim 1, wherein said fluorescent light processing and analysis apparatus comprises:
fluorescent light processing apparatus that processes said fluorescent light exiting the side of the segment of glass to produce processed fluorescent light; and
fluorescent light analysis apparatus that analyzes the processed fluorescent light to derive information indicative of the thickness of the segment of glass.

15. As apparatus as defined in claim 14, wherein said fluorescent light processing apparatus additionally comprises:
a filter that passes fluorescent light but not light at the frequency of said light beam source, said filter being located intermediate the side of the segment of glass and said fluorescent light analysis apparatus.

16. As apparatus as defined in claim 15, wherein said filter comprises:
one of the group consisting of a long pass filter that passes fluorescent light, a band pass filter that passes fluorescent light, and a notch filter that passes fluorescent light.

17. As apparatus as defined in claim 14, wherein said fluorescent light analysis apparatus comprises:
a camera for acquiring an image of the modulated linearly polarized portion of said fluorescent light exiting the side of the segment of glass.

18. As apparatus as defined in claim 17, wherein said fluorescent light analysis apparatus additionally comprises:
an image processor for processing said image of the modulated linearly polarized portion of said fluorescent light exiting the side of the segment of glass to produce a line the length of which represents the thickness of the segment of glass.

19. As apparatus as defined in claim 14, wherein said fluorescent light processing apparatus comprises:
a quarter wave plate located intermediate said fluorescent light coupling apparatus and said fluorescent light analysis apparatus to linearly polarize said fluorescent light exiting the side of the segment of glass, wherein said quarter wave plate has an axis that is aligned at an angle of approximately 45 degrees with respect to a linearly polarized portion of said fluorescent light exiting the side of the segment of glass;
and wherein said fluorescent light processing apparatus additionally comprises:
a polarization rotator located intermediate said quarter wave plate and said fluorescent light analysis apparatus for alternately modulating the polarization state of the linearly polarized portion of said fluorescent light exiting the side of the segment of glass plus and minus 45 degrees with respect to said axis of said quarter wave plate;
and wherein said fluorescent light analysis apparatus further comprises:
a camera for acquiring a first image through said polarization rotator of the modulated linearly polarized portion of said fluorescent light exiting the side of the segment of glass at plus 45 degrees with respect to said axis of said quarter wave plate and a second image through said polarization rotator of the modulated linearly polarized portion of said fluorescent light exiting the side of the segment of glass at minus 45 degrees with respect to said axis of said quarter wave plate;
an image differentiator for differentiating said first and second images to produce a normalized difference image characteristic of the thickness of the segment of glass; and
an image processor for processing said normalized difference image to produce a line the length of which represents the thickness of the segment of glass.

20. As apparatus as defined in claim 16, wherein said polarization rotator comprises:
a rotator drive producing alternating positive and negative voltages; and
a ferroelectric liquid crystal element that is driven by said alternating positive and negative voltages from said rotator drive.

21. As apparatus as defined in claim 19, wherein said fluorescent light processing apparatus additionally comprises:
a long pass filter that passes fluorescent light, said long pass filter being located intermediate said ferroelectric liquid crystal element and said camera.

22. As apparatus as defined in claim 1, additionally comprising:
scanning apparatus for moving said apparatus for measuring the thickness of the segment of glass to a plurality of positions adjacent different locations on the side of the segment of glass.

23. An apparatus for measuring the thickness of a segment of glass, comprising:
a light beam source that generates a linearly polarized light beam;
light beam coupling apparatus for directing said linearly polarized light beam at the side of a segment of glass at an angle facilitating entry of said light beam into and through the side of the segment of glass, said linearly polarized light beam causing fluorescent light to be emitted within the segment of glass in response to said linearly polarized light beam within the segment of glass;
fluorescent light coupling apparatus for coupling a portion of said fluorescent light emitted in response to said linearly polarized light beam within the segment of glass outwardly from the side of the segment of glass;
a camera for acquiring images of the processed fluorescent light exiting the side of the segment of glass; and
fluorescent light analysis apparatus that analyzes the processed fluorescent light to derive information indicative of the thickness of the segment of glass.

24. An apparatus for measuring the thickness of a segment of glass, comprising:
a light beam source that generates a light beam;
light beam coupling apparatus for directing said light beam at the side of a segment of glass at an angle facilitating entry of said light beam into and through the side of the segment of glass, said light beam causing fluorescent light to be emitted within the segment of glass in response to said light beam within the segment of glass;
fluorescent light coupling apparatus for coupling a portion of said fluorescent light emitted in response to said light beam within the segment of glass outwardly from the side of the segment of glass; and fluorescent light processing apparatus that processes the fluorescent light exiting the side of the glass container to determine the thickness of the segment of glass.

25. A method for measuring the thickness of a segment of glass, comprising:

directing a light beam at the side of a glass container at an angle facilitating entry of the light beam into and through the side of the segment of glass;

detecting fluorescent light emitted in response to the light beam within the segment of glass which fluorescent light exits the side of the segment of glass; and processing the fluorescent light exiting the side of the segment of glass and analyzing the processed fluorescent light exiting the side of the segment of glass to determine the thickness of the segment of glass.

* * * * *